(12) United States Patent
McGowan et al.

(10) Patent No.: US 11,840,532 B2
(45) Date of Patent: Dec. 12, 2023

(54) MODULATORS OF THR-β AND METHODS OF USE THEREOF

(71) Applicant: ALIGOS THERAPEUTICS, INC., South San Francisco, CA (US)

(72) Inventors: David Craig McGowan, Brussels (BE); Pierre Jean-Marie Bernard Raboisson, Wavre (BE); Koen Vandyck, Paal (BE); Jerome Deval, El Granada, CA (US)

(73) Assignee: Aligos Therapeutics, Inc., South San Francisco, CA (US)

(*) Notice: Subject to any disclaimer, the term of this patent is extended or adjusted under 35 U.S.C. 154(b) by 148 days.

(21) Appl. No.: 17/370,623

(22) Filed: Jul. 8, 2021

(65) Prior Publication Data

US 2022/0009924 A1 Jan. 13, 2022

Related U.S. Application Data

(60) Provisional application No. 63/050,447, filed on Jul. 10, 2020.

(51) Int. Cl.
*C07D 471/04* (2006.01)
*A61K 45/06* (2006.01)
*A61P 1/16* (2006.01)

(52) U.S. Cl.
CPC ............ *C07D 471/04* (2013.01); *A61K 45/06* (2013.01); *A61P 1/16* (2018.01)

(58) Field of Classification Search
CPC .................................................. C07D 471/04
USPC ......................................................... 514/300
See application file for complete search history.

(56) References Cited

U.S. PATENT DOCUMENTS

| | | | | |
|---|---|---|---|---|
| 6,326,398 B1 * | 12/2001 | Chiang | ................... | A61P 27/06 564/155 |
| 6,794,406 B2 * | 9/2004 | Haning | ................ | C07D 209/08 514/369 |
| 7,230,031 B2 * | 6/2007 | Shiohara | .............. | C07D 237/14 514/557 |
| 2003/0078288 A1 | 4/2003 | Haning et al. | | |

FOREIGN PATENT DOCUMENTS

WO          2001070687      *  9/2001
WO      WO-2021/041237 A1      3/2021

OTHER PUBLICATIONS

Haning et al., Bioorganic & Medicinal Chemistry Letters (2005), 15(7), 1835-1840.*
Joharapurkar et al., Journal of Medicinal Chemistry (2012), 55(12), 5649-5675.*

Bookout et al., "Anatomical Profiling of Nuclear Receptor Expression Reveals a Hierarchical Transcriptional Network," Cell, Aug. 25, 2006, 126(4):789-799.
Chalasani et al., "The Diagnosis and Management of Non-alcoholic Fatty Liver Disease: Practice Guideline by the American Gastroenterological Association, American Association for the Study of Liver Diseases, and American College of Gastroenterology," Gastroenterology, 2012, 142:1592-1609.
Dulai et al., "Increased Risk of Mortality by Fibrosis Stage in Nonalcoholic Fatty Liver Disease: Systematic Review and Meta-Analysis," Hepatology, May 2017, 65(5):1557-1565.
Erion et al., "Targeting thyroid hormone receptor-B agonists to the liver reduces cholesterol and triglycerides and improves the therapeutic index," PNAS, Sep. 25, 2007, 104(39):15490-15495.
Flamant et al., "International Union of Pharmacology. LIX. The Pharmacology and Classification of the Nuclear Receptor Superfamily: Thyroid Hormone Receptors," Pharmacological Reviews, 2006, 58(4):705-711.
Haning et al., "Novel heterocyclic thryomimetics," Bioorganic & Medicinal Chemistry Letters, Apr. 1, 2005, 15(7):1835-1840.
Hartley et al., "A Thyroid Hormone-Based Strategy for Correcting the Biochemical Abnormality in X-Linked Adrenoleukodystrophy," Endocrinology, May 2017, 158(5):1328-1338.
Harvey et al., "Mechanism of Thyroid Hormone Action," Thyroid, Jun. 2002, 12(6):441-446.
Hirano et al., "Thyromimetics: a review of recent reports and patents (2004-2009)," Expert Opin. Ther. Pat., Feb. 2010, 20(2):213-228.
International Search Report and Written Opinion dated Oct. 19, 2021 in PCT/US2021/040855.
Kowalik et al., "Thyroid Hormones, Thyromimetics and Their Metabolites in the Treatment of Liver Disease," Frontiers in Endocrinology, Jul. 10, 2018, 9:382, 11 pages.
Lazo et al., "Nonalcoholic Fatty Liver disease (NAFLD): Is It Really a Serious Condition?", Hepatology, Oct. 2012, 56(4):1580-1584.
Malm et al., "Recent Advances in the Development of Agonists Selective for Beta1-Type Thyroid Hormone Receptor," Mini-Reviews in Medicinal Chemistry, 2007, 7(1):79-86.
Malm, Johan, "Thyroid Hormone Ligands and Metabolic Diseases," Current Pharmaceutical Design, 2004, 10(28):3525-3532.

(Continued)

*Primary Examiner* — Niloofar Rahmani
(74) *Attorney, Agent, or Firm* — Foley & Lardner LLP

(57) ABSTRACT

Disclosed herein are compounds of Formula I':

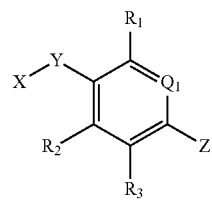

Formula I' or a stereoisomer or a tautomer thereof, or a pharmaceutically acceptable salt thereof, pharmaceutical compositions comprising such compounds, and methods of treating disease by administering or contacting a patient with one or more of the above compounds.

12 Claims, No Drawings

(56) References Cited

OTHER PUBLICATIONS

Milanesi et al., "Beam Me In: Thyroid Hormone Analog Targets Alternative Transporter in Mouse Model of X-Linked Adrenoleukodystrophy," Endocrinology, May 2017, 158:1116-1119.

Serfaty et al., "Definition and natural history of metabolic steatosis: clinical aspects of NAFLD, NASH and cirrhosis," Diabetes and Metabolism, 2008, 34:634-637.

Younossi et al., "Current and Future Therapeutic Regimens for Nonalcoholic Fatty Liver Disease and Nonalcoholic Steatohepatitis," Hepatology, Jul. 2018, 68(1):361-371.

Younossi et al., "Global Epidemiology of Nonalcoholic Fatty Liver Disease—Meta-Analytic Assessment of Prevalence, Incidence and Outcomes," Hepatology, Jul. 2016, 64(1):73-84.

\* cited by examiner

MODULATORS OF THR-β AND METHODS OF USE THEREOF

CROSS-REFERENCE TO RELATED APPLICATIONS

This application claims the benefit of priority to U.S. Provisional Patent Application Ser. No. 63/050,447, filed on Jul. 10, 2020, the entire disclosure of which is hereby incorporated by reference herein.

FIELD OF THE DISCLOSURE

The present disclosure is in the field of pharmaceutical compounds and preparations and method of their use in the treatment of disease. In particular, the present disclosure is in the field of THR-I3 modulators and their use.

BACKGROUND OF THE DISCLOSURE

In parallel with the global increase in obesity, nonalcoholic fatty liver disease (NAFLD) is becoming the leading cause of chronic liver disease and liver transplantation worldwide [1,2]. NAFLD is believed to affect 30% of the adult population and 70-80% of individuals who are obese and diabetic. NAFLD is defined as excess liver fat accumulation greater than 5% induced by causes other than alcohol intake. NAFLD progresses to liver inflammation (nonalcoholic steatohepatitis, NASH) and fibrosis in a variable proportion of individuals, ultimately leading to liver failure and hepatocellular carcinoma (HCC) in susceptible individuals [3].

In the United States alone, NASH is the third most common indication for liver transplantation and is on a trajectory to become the most common [4]. The most important medical need in patients with NAFLD and NASH is an effective treatment to halt the progression and possibly reverse fibrosis, which is the main predictor of liver disease evolution [5,6].

Thyroid hormone (TH) is essential for normal development, growth and metabolism of all vertebrates. Its effects are mediated principally through triiodothyronine (T3), which acts as a ligand for the TH receptors (TRs, or THRs) β1, β2 and α[7]. In the absence of ligand, TR first binds as a heterodimer or homodimer on TH response elements (TRE) located in the promoter regions of target genes, where it interacts with corepressors. Upon ligand binding, the TR homodimers are dissociated in favor of heterodimer formation with the retinoid-X receptor (RXR), resulting in release of the corepressors and recruitment of coactivators. This new complex attracts a large number of proteins which engage the RNA polymerase II in the transcription of the targeted genes.

Two different genetic loci, denoted THRA and THRB, are responsible for encoding multiple interrelated TR isoforms that have distinct tissue distributions and biological functions. The two major isoforms with the broadest level of tissue expression are TRα1 and TRβ1 [8]. While TRα1 is expressed first during fetal development and is widely expressed in adult tissues, TRβ1 appears later in development and displays highest expression in the adult liver, kidney, and lung [9]. TRα1 is a key regulator of cardiac output, whereas TRβ1 helps in the control of metabolism in the liver. Importantly, the natural thyroid hormone T3 activates both TRα1 and TRβ1 without any significant selectivity.

Design of thyromimetic small molecule agents led to the identification of TR (or THR) agonists with varying levels of TRβ selectivity despite high structural similarity between the ligand-binding domains for TRβ and TRα. TRβ selectivity achieved by some of these compounds resulted in an improved therapeutic index for lipid lowering relative to cardiac effects such as heart rate, cardiac hypertrophy, and contractility [10-12].

Another strategy to avoid activation of TRα in cardiac tissue is to design prodrugs of phosphonate-containing TR agonists that are specifically converted to the active agonist in the liver but remain stable as an inactive prodrug in blood and extrahepatic tissues, including the heart [13]. TRα and TRβ agonists are also used in indications other than liver-related disorders, as has been known in the art. For example, TRβ selective agonists may be useful in the treatment of X-linked adrenoleukodystrophy [14, 15].

SUMMARY

Disclosed herein are compounds of Formula I' :

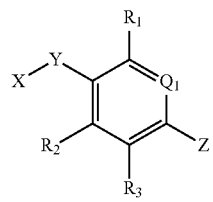

Formula I' or a stereoisomer or a tautomer thereof, or a pharmaceutically acceptable salt thereof, wherein $Q_1$ is CH or N;

$R_1$ and $R_2$ are each independently selected from hydrogen, halogen, cyclopropyl, and $C_{1-3}$ alkyl optionally substituted with 1 to 5 fluorine;

$R_3$ is selected from hydrogen, deuterium, halogen, —CN, $C_{1-10}$ alkoxy, and $C_{1-6}$ alkyl; or $R_2$ and $R_3$ taken together along with the carbon atoms to which they are attached form a 4- to 6-membered carbocyclic ring or a four- to six-membered heterocyclic ring;

X is

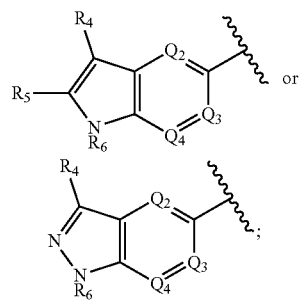

$R_4$ is selected from hydrogen; $C_1$-$C_6$ alkyl; a non-aromatic $C_3$-$C_{12}$ carbocyclic ring; a $C_6$-$C_{10}$ aryl group; a (carbocyclic)alkyl group; and an aralkyl group; wherein $R_4$ is optionally substituted with one to three $R_k$ independently selected from halogen, —CN, $C_1$-$C_6$ alkyl, $C_1$-$C_6$ alkoxy, $C_1$-$C_6$ haloalkyl, and $C_1$-$C_6$ haloalkoxy; and R₅ is selected from hydrogen; halogen; $C_1$-$C_6$ alkyl optionally substituted with halogen or $C_1$-$C_6$ alkoxy; and $C_3$-$C_9$ cycloalkyl optionally substituted with halogen or $C_1$-$C_6$ alkoxy; or R₄ and R₅ taken together along with the carbon atoms to which they are attached form a 4- to 6-membered carbocyclic ring;

R₆ is hydrogen or $C_1$-$C_3$ alkyl;

Q₂, Q₃, and Q₄ are each independently selected from CH or N, and at least one of Q₂, Q₃, and Q₄ must be N; Y is O or $CH_2$;

Z is selected from the group consisting of:

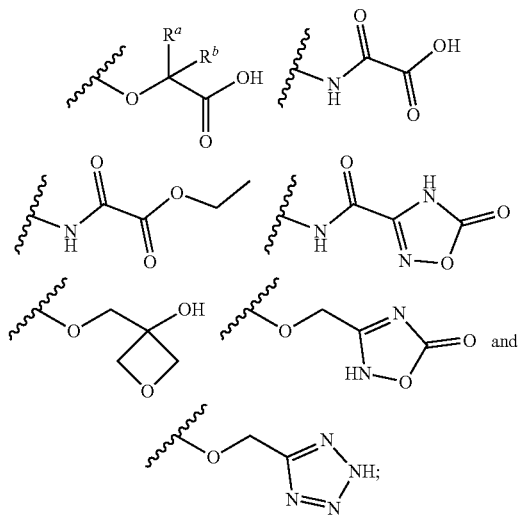

and

Rᵃ and Rᵇ are each independently selected from hydrogen, methyl, and fluorine;

with the proviso that when X is

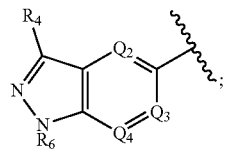

Q₁ is CH; R₁ and R₂ are each independently halogen; R₃ is hydrogen; R₄ is $C_1$-$C_6$ alkyl; R₆ is hydrogen; Q₂ is CH; Q₃ is CH; Q₄ is N; and Y is O; then Z is selected from the group consisting of:

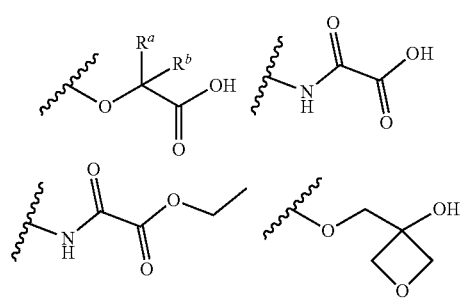

-continued

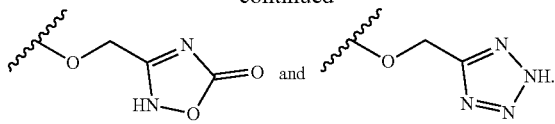

Disclosed herein are compounds of Formula I:

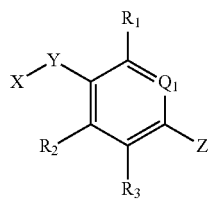

Formula I or a stereoisomer or a tautomer thereof, or a pharmaceutically acceptable salt thereof, wherein Q₁ is CH or N;

R₁ and R₂ are each independently selected from hydrogen, halogen, cyclopropyl, and $C_{1-3}$ alkyl optionally substituted with 1 to 5 fluorine;

R₃ is selected from hydrogen, deuterium, halogen, —CN, $C_{1-10}$ alkoxy, and $C_{1-6}$ alkyl; or R₂ and R₃ taken together along with the carbon atoms to which they are attached form a 4- to 6-membered carbocyclic ring or a four- to six-membered heterocyclic ring;

X is an optionally substituted 6- to 10-membered heterocycle;

Y is O or $CH_2$;

Z is selected from the group consisting of:

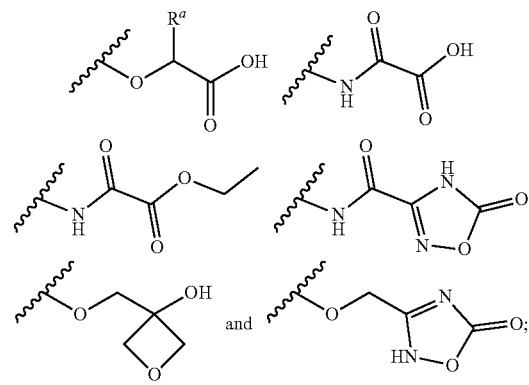

and

Rᵃ is selected from hydrogen, methyl, and fluorine.

In some embodiments, X is:

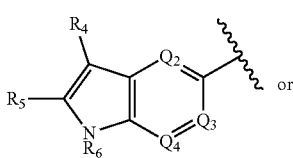

-continued

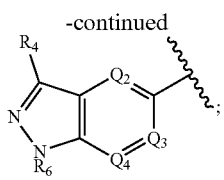

wherein
$R_4$ is selected from hydrogen; $C_1$-$C_6$ alkyl; a non-aromatic $C_3$-$C_{12}$ carbocyclic ring; a $C_6$-$C_{10}$ aryl group; a (carbocyclic)alkyl group; and an aralkyl group; and
$R_4$ is optionally substituted with one to three $R_k$ independently selected from halogen, —CN, $C_1$-$C_6$ alkyl, $C_1$-$C_6$ alkoxy, $C_1$-$C_6$ haloalkyl, and $C_1$-$C_6$ haloalkoxy;
$R_5$ is selected from hydrogen; halogen; $C_1$-$C_6$ alkyl optionally substituted with halogen or $C_1$-$C_6$ alkoxy; and $C_3$-$C_9$ cycloalkyl optionally substituted with halogen or $C_1$-$C_6$ alkoxy;
$R_6$ is hydrogen or $C_1$-$C_3$ alkyl; and
$Q_2$, $Q_3$, and $Q_4$ are each independently selected from CH or N, and at least one of $Q_2$, $Q_3$, and $Q_4$ must be N.

In some embodiments, X is:

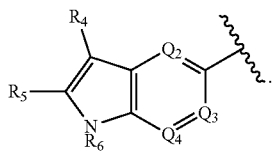

In some embodiments, X is:

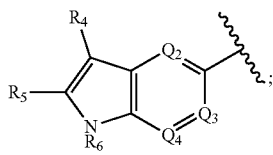

$R_4$ is selected from hydrogen; $C_1$-$C_6$ alkyl; a non-aromatic $C_3$-$C_{12}$ carbocyclic ring; a $C_6$-$C_{10}$ aryl group; a (carbocyclic)alkyl group; and an aralkyl group; wherein $R_4$ is optionally substituted with one to three $R_k$ independently selected from halogen, —CN, $C_1$-$C_6$ alkyl, $C_1$-$C_6$ alkoxy, $C_1$-$C_6$ haloalkyl, and $C_1$-$C_6$ haloalkoxy;
$R_5$ is selected from hydrogen; halogen; $C_1$-$C_6$ alkyl optionally substituted with halogen or $C_1$-$C_6$ alkoxy; and $C_3$-$C_9$ cycloalkyl optionally substituted with halogen or $C_1$-$C_6$ alkoxy;
$R_6$ is hydrogen or $C_1$-$C_3$ alkyl; and
$Q_2$, $Q_3$, and $Q_4$ are each independently selected from CH or N, and at least one of $Q_2$, $Q_3$, and $Q_4$ must be N.

In some embodiments, X is:

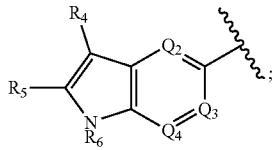

$R_4$ and $R_5$ taken together along with the carbon atoms to which they are attached form a 4- to 6-membered carbocyclic ring;
$R_6$ is hydrogen or $C_1$-$C_3$ alkyl; and
$Q_2$, $Q_3$, and $Q_4$ are each independently selected from CH or N, and at least one of $Q_2$, $Q_3$, and $Q_4$ must be N.

DETAILED DESCRIPTION

Disclosed herein are novel compounds that are effective modulators of THR-β activity that can be used for the treatment of various THR-β related disorders. The compounds and the methods of their use are discussed in detail below. Certain of the compounds disclosed herein are agonists, while others are antagonists, of TRα and/or TRβ receptors and are used to treat liver-related disorders and other indications known in the art that are mediated by TRα and/or TRβ receptors.

Definitions

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In the definition of chemical substituents, each of $R_x$ and $R_y$ is independently hydrogen, alkyl, carbocyclic ring, heterocyclic ring, aryl, or heteroaryl, all of which, except hydrogen, are optionally substituted.

Unless otherwise indicated, the abbreviations "TR" and "THR" refer to thyroid hormone receptors.

As used herein, "pharmaceutically acceptable salt" refers to a salt of a compound that does not cause significant irritation to a patient to which it is administered and does not abrogate the biological activity and properties of the compound. Pharmaceutical salts can be obtained by reaction of a compound disclosed herein with an acid or base. Base-formed salts include, without limitation, ammonium salt ($NH_4^+$); alkali metal, such as, without limitation, sodium or potassium, salts; alkaline earth, such as, without limitation, calcium or magnesium, salts; salts of organic bases such as, without limitation, dicyclohexylamine, N-methyl-D-glucamine, tris(hydroxymethyl)methylamine; and salts with the amino group of amino acids such as, without limitation, arginine and lysine. Useful acid-based salts include, without limitation, hydrochlorides, hydrobromides, sulfates, nitrates, phosphates, methane-sulfonates, ethanesulfonates, p-toluenesulfonates and salicylates.

As used herein, "pharmaceutically acceptable ester" refers to an ester of a compound that does not cause significant irritation to a patient to which it is administered. The ester is metabolized in the body to result in the parent compound, e.g., the claimed compound. Accordingly, the ester does not abrogate the biological activity and properties of the compound. Pharmaceutical esters can be obtained by reaction of a compound disclosed herein with an alcohol. Methyl, ethyl, and isopropyl esters are some of the common esters to be prepared. Other esters suitable are well-known to those skilled in the art (see, for example Wuts, P. G. M., Greene's Protective Groups in Organic Synthesis, 5$^{th}$ Ed., John Wiley & Sons, New York, N.Y., 2014, which is incorporated herein by reference in its entirety).

Where the compounds disclosed herein have at least one chiral center, they may exist as a racemate or as individual enantiomers. It should be noted that all such isomers and mixtures thereof are included in the scope of the present disclosure. Thus, the illustration of a chiral center without a designation of R or S signifies that the scope of the disclosure includes the R isomer, the S isomer, the racemic mixture of the isomers, or mixtures where one isomer is present in greater abundance than the other.

Where the processes for the preparation of the compounds disclosed herein give rise to mixtures of stereoisomers, such isomers may be separated by conventional techniques such as preparative chiral chromatography. The compounds may be prepared in racemic form or individual enantiomers may be prepared by stereoselective synthesis or by resolution. The compounds may be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides followed by chromatographic separation and removal of the chiral auxiliary.

Unless otherwise indicated, when a substituent is deemed to be "optionally substituted" it is meant that the substituent is a group that may be substituted with one or more (e.g., 1 to 2, or 1 to 3, or 1 to 4, or 1 to 5, or 1 to 6) group(s) individually and independently selected, without limitation, from alkyl, alkenyl, alkynyl, cycloalkyl, aryl, heteroaryl, heteroalicyclic, hydroxy, alkoxy, aryloxy, mercapto, alkylthio, arylthio, cyano, halo, carbonyl, thiocarbonyl, O-carbamoyl, N-carbamoyl, O-thiocarbamoyl, N-thiocarbamoyl, C-amido, N-amido, S-sulfonamido, N-sulfonamido, C-carboxy, O-carboxy, is O-cyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Wuts, above.

As used herein, a "carbocyclic ring" is a ring structure in which all the atoms in the ring are carbon atoms. If any of the atoms in the ring is anything other than a carbon atom, then the ring is a "heterocyclic ring." Examples of atoms that are within a ring include sulfur, oxygen, and nitrogen. A carbocyclic ring or a heterocyclic ring may be polycyclic, e.g., a fused ring system, a spirocyclic ring system, or a bridged ring system. These polycyclic rings include, for example, adamantyl, norbornyl (i.e., bicyclo[2.2.1]heptanyl), norbornenyl, decalinyl, 7,7-dimethyl-bicyclo[2.2.1]heptanyl, and the like. Additional non-limiting examples include:

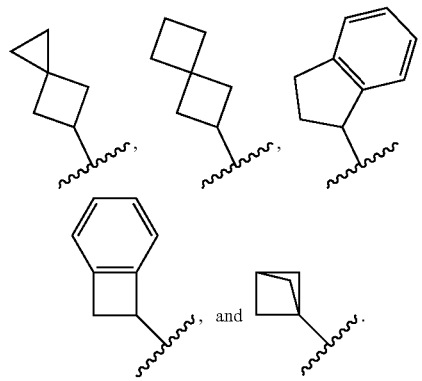

As used herein, "aryl" refers to a carbocyclic (all carbon) ring that has a fully delocalized pi-electron system. The "aryl" group can be made up of two or more fused rings (rings that share two adjacent carbon atoms). When the aryl is a fused ring system, then the ring that is connected to the rest of the molecule has a fully delocalized pi-electron system. The other ring(s) in the fused ring system may or may not have a fully delocalized pi-electron system. Examples of aryl groups include, without limitation, the radicals of benzene, naphthalene and azulene. Additional non-limiting examples include:

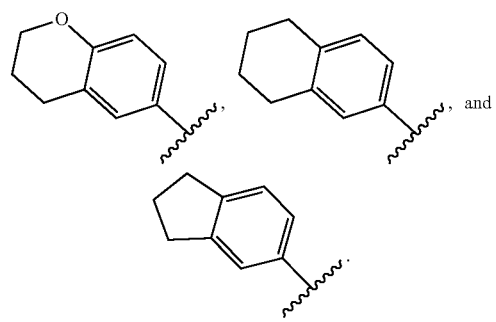

As used herein, "heteroaryl" refers to a ring that has a fully delocalized pi-electron system and contains one or more heteroatoms selected from the group consisting of nitrogen, oxygen, and sulfur in the ring. The "heteroaryl" group can be made up of two or more fused rings (rings that share two adjacent carbon atoms). When the heteroaryl is a fused ring system, then the ring that is connected to the rest of the molecule has a fully delocalized pi-electron system. The other ring(s) in the fused ring system may or may not have a fully delocalized pi-electron system. Examples of heteroaryl rings include, without limitation, furan, thiophene, phthalazinone, pyrrole, oxazole, thiazole, imidazole, pyrazole, isoxazole, isothiazole, triazole, thiadiazole, pyridine, pyridazine, pyrimidine, pyrazine and triazine.

Wherever "hetero" is used it is intended to mean a group as specified, such as an alkyl or an aryl group, where at least one carbon atom has been replaced with a heteroatom selected from nitrogen, oxygen and sulfur.

As used herein, "alkyl" refers to a straight or branched chain fully saturated (no double or triple bonds) hydrocarbon group. An alkyl group of the presently disclosed compounds may comprise from 1 to 20 carbon atoms. An alkyl group herein may also be of medium size having 1 to 10 carbon atoms. An alkyl group herein may also be a lower alkyl having 1 to 5 carbon atoms. Examples of alkyl groups include, without limitation, methyl, ethyl, n-propyl, isopropyl, n-butyl, i-butyl, sec-butyl, t-butyl, amyl, t-amyl, hexyl, heptyl, octyl, nonyl, decyl, undecyl and dodecyl.

An alkyl group of the presently disclosed compounds may be substituted or unsubstituted. When substituted, the substituent group(s) can be one or more group(s) independently selected from cycloalkyl, aryl, heteroaryl, heteroalicyclyl, hydroxy, protected hydroxy, alkoxy, aryloxy, mercapto, alkylthio, arylthio, cyano, halogen, carbonyl, thiocarbonyl, O-carbamoyl, N-carbamoyl, O-thiocarbamoyl, N-thiocarbamoyl, C-amido, N-amido, S-sulfonamido, N-sulfonamido, C-carboxy, protected C-carboxy, O-carboxy, isocyanato, thiocyanato, isothiocyanato, nitro, silyl, trihalomethanesulfonyl, —$NR_xR_y$ and protected amino.

As used herein, "alkenyl" refers to an alkyl group that contains in the straight or branched hydrocarbon chain one or more double bonds. An alkenyl group of the presently disclosed compounds may comprise from 2 to 20 carbon atoms. An alkenyl group herein may also be of medium size having 2 to 10 carbon atoms. An alkenyl group herein may also be a lower alkenyl having 2 to 5 carbon atoms or 2 to 6 carbon atoms. An alkenyl group of the presently disclosed compounds may be unsubstituted or substituted. When substituted, the substituent(s) may be selected from the same groups disclosed above regarding alkyl group substitution, or with regard to optional substitution.

As used herein, "alkynyl" refers to an alkyl group that contains in the straight or branched hydrocarbon chain one or more triple bonds. An alkynyl group of the presently disclosed compounds may comprise from 2 to 20 carbon atoms. An alkynyl group herein may also be of medium size having 2 to 10 carbon atoms. An alkynyl group herein may also be a lower alkynyl having 2 to 5 carbon atoms or 2 to 6 carbon atoms. An alkynyl group of the presently disclosed compounds may be unsubstituted or substituted. When substituted, the substituent(s) may be selected from the same groups disclosed above regarding alkyl group substitution, or with regard to optional substitution.

As used herein, "alkoxy" refers to an "—O-(alkyl)" group, wherein "alkyl" is as defined above.

As used herein, "acyl" refers to an "$R_xC(=O)$—" group.

As used herein, "cycloalkyl" refers to a completely saturated (no double bonds) hydrocarbon ring. Cycloalkyl groups of the presently disclosed compounds may range from $C_3$ to $C_8$. A cycloalkyl group may be unsubstituted or substituted. If substituted, the substituent(s) may be selected from those indicated above regarding substitution of an alkyl group. The "cycloalkyl" group can be made up of two or more fused rings (rings that share two adjacent carbon atoms). When the cycloalkyl is a fused ring system, then the ring that is connected to the rest of the molecule is a cycloalkyl as defined above. The other ring(s) in the fused ring system may be a cycloalkyl, a cycloalkenyl, an aryl, a heteroaryl, or a heteroalicyclic.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). A cycloalkenyl group of the presently disclosed compounds may unsubstituted or substituted. When substituted, the substituent(s) may be selected from the same groups disclosed above regarding alkyl group substitution. The "cycloalkenyl" group can be made up of two or more fused rings (rings that share two adjacent carbon atoms). When the cycloalkenyl is a fused ring system, then the ring that is connected to the rest of the molecule is a cycloalkenyl as defined above. The other ring(s) in the fused ring system may be a cycloalkyl, a cycloalkenyl, an aryl, a heteroaryl, or a heteroalicyclic.

The term "alkylene" refers to an alkyl group, as defined herein, which is a biradical and is connected to two other moieties. Thus, methylene (—$CH_2$—), ethylene (—$CH_2CH_2$—), propylene (—$CH_2CH_2CH_2$—), isopropylene (IUPAC: (methyl)ethylene) (—$CH_2$—$CH(CH_3)$—), and isobutylene (IUPAC: 2-(methyl)propylene) (—$CH_2$—$CH(CH_3)$—$CH_2$—) are examples, without limitation, of an alkylene group. Similarly, the term "cycloalkylene" refers to a cycloalkyl group, as defined here, which binds in an analogous way to two other moieties. If the alkyl and cycloalkyl groups contain unsaturated carbons, the terms "alkenylene" and "cycloalkenylene" are used.

As used herein, "heterocycloalkyl," "heteroalicyclic," or "heteroali-cyclyl" refers to a ring having in the ring system one or more heteroatoms independently selected from nitrogen, oxygen and sulfur. The ring may also contain one or more double bonds provided that they do not form a fully delocalized pi-electron system in the rings. The ring defined herein can be a stable 3- to 18-membered ring that consists of carbon atoms and from one to five heteroatoms selected from the group consisting of nitrogen, oxygen, and sulfur. Heteroalicyclyl groups of the presently disclosed compounds may be unsubstituted or substituted. When substituted, the substituent(s) may be one or more groups independently selected from the group consisting of halogen, hydroxy, protected hydroxy, cyano, nitro, alkyl, alkoxy, acyl, acyloxy, carboxy, protected carboxy, amino, protected amino, carboxamide, protected carboxamide, alkylsulfonamido and trifluoromethane-sulfonamido. The "heterocycloalkyl" group can be made up of two or more fused rings (rings that share two adjacent carbon atoms). When the heterocycloalkyl is a fused ring system, then the ring that is connected to the rest of the molecule is a heterocycloalkyl as defined above. The other ring(s) in the fused ring system may be a cycloalkyl, a cycloalkenyl, an aryl, a heteroaryl, or a heteroalicyclic.

As used herein, "aralkyl" refers to an alkylene substituted with an aryl group.

As used herein, "(carbocyclic)alkyl" refers to an alkylene substituted with a carbocyclic group.

As used herein, (heterocyclic)alkyl" refers to an alkylene substituted with a heterocyclic group.

As used herein, "(heteroaryl)alkyl" refers to an alkylene substituted with a heteroaryl group.

An "O-carboxy" group refers to a "$R_xC(=O)O$—" group.

A "C-carboxy" group refers to a "—$C(=O)R$" group.

An "acetyl" group refers to a $CH_3C(=O)$-group.

A "C-amido" group refers to a "—$C(=O)NR_xR_y$" group.

An "N-amido" group refers to a "$RC(=O)NR_x$-" group.

The term "perhaloalkyl" refers to an alkyl group in which all the hydrogen atoms are replaced by halogen atoms.

Any unsubstituted or monosubstituted amine group on a compound herein can be converted to an amide, any hydroxy group can be converted to an ester and any carboxyl group can be converted to either an amide or ester using techniques well-known to those skilled in the art (see, for example Wuts, above).

It is understood that, in any compound of the presently disclosed compounds having one or more chiral centers, if an absolute stereochemistry is not expressly indicated, then each center may independently be R or S or a mixture thereof. In addition, it is understood that, in any compound of the presently disclosed compounds having one or more double bond(s) generating geometrical isomers that can be defined as E or Z each double bond may independently be E or Z, or a mixture thereof.

It is understood that the disclosure of a compound herein inherently includes the disclosure of a tautomer thereof, if applicable. For instance, the disclosure of:

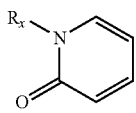

also includes the disclosure of:

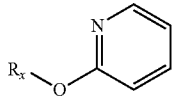

and vice versa, even if only one of the two structures is disclosed.

Throughout the present disclosure, when a compound is illustrated or named, it is understood that the isotopically enriched analogs of the compound are also contemplated. For example, a compound may have a deuterium incorporated instead of a hydrogen, or a carbon-13 instead of carbon with natural isotopic distribution. The isotopic enrichment may be in one location on the compound, i.e., only one hydrogen is replaced by a deuterium, or in more than one location. The present disclosure also encompasses compounds where all the similar atoms are replaced by their less common isotope, for example, a perdeutero compound where all the hydrogen atoms are replaced by a deuterium. The isotopically enriched compounds are useful when obtaining NMR spectra or when making use of an isotope effect in managing the kinetics of the reaction the compound undergoing.

The term "pharmaceutical composition" refers to a mixture of one or more compounds disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example, dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

In certain embodiments, the same substance can act as a carrier, diluent, or excipient, or have any of the two roles, or have all three roles. Thus, a single additive to the pharmaceutical composition can have multiple functions.

The term "pharmaceutically acceptable" defines a carrier or diluent that does not abrogate the biological activity and properties of the compound.

Compounds

In one aspect, disclosed herein are compounds of Formula I':

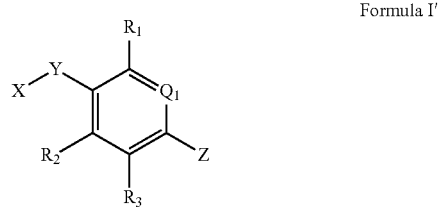

Formula I' or a stereoisomer or a tautomer thereof, or a pharmaceutically acceptable salt thereof, wherein $Q_1$ is CH or N;

$R_1$ and $R_2$ are each independently selected from hydrogen, halogen, cyclopropyl, and $C_{1-3}$ alkyl optionally substituted with 1 to 5 fluorine;

$R_3$ is selected from hydrogen, deuterium, halogen, —CN, $C_{1-10}$ alkoxy, and $C_{1-6}$ alkyl; or $R_2$ and $R_3$ taken together along with the carbon atoms to which they are attached form a 4- to 6-membered carbocyclic ring or a four- to six-membered heterocyclic ring;

X is

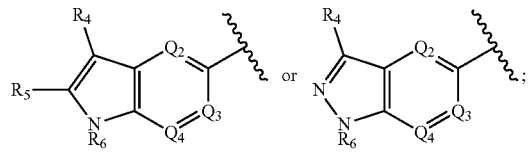

$R_4$ is selected from hydrogen; $C_1$-$C_6$ alkyl; a non-aromatic $C_3$-$C_{12}$ carbocyclic ring; a $C_6$-$C_{10}$ aryl group; a (carbocyclic)alkyl group; and an aralkyl group; wherein $R_4$ is optionally substituted with one to three $R_k$ independently selected from halogen, —CN, $C_1$-$C_6$ alkyl, $C_1$-$C_6$ alkoxy, $C_1$-$C_6$ haloalkyl, and $C_1$-$C_6$ haloalkoxy; and $R_5$ is selected from hydrogen; halogen; $C_1$-$C_6$ alkyl optionally substituted with halogen or $C_1$-$C_6$ alkoxy; and $C_3$-$C_9$ cycloalkyl optionally substituted with halogen or $C_1$-$C_6$ alkoxy; or $R_4$ and $R_5$ taken together along with the carbon atoms to which they are attached form a 4- to 6-membered carbocyclic ring;

$R_6$ is hydrogen or $C_1$-$C_3$ alkyl;

$Q_2$, $Q_3$, and $Q_4$ are each independently selected from CH or N, and at least one of $Q_2$, $Q_3$, and $Q_4$ must be N; Y is O or $CH_2$;

Z is selected from the group consisting of:

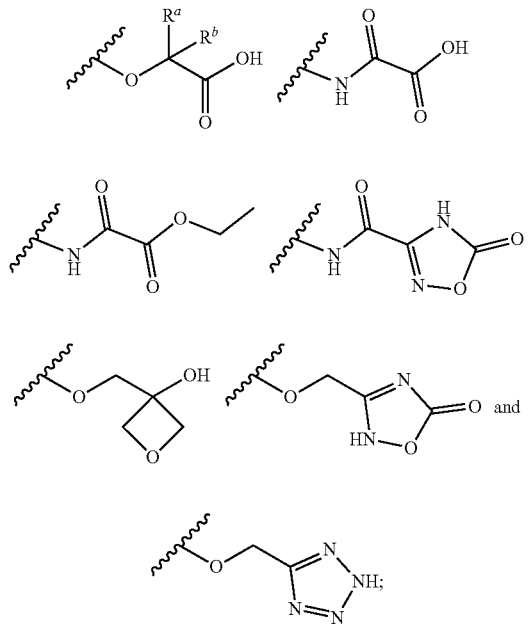

and $R^a$ and $R^b$ are each independently selected from hydrogen, methyl, and fluorine;

with the proviso that when X is

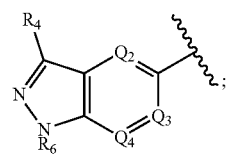

$Q_1$ is CH; $R_1$ and $R_2$ are each independently halogen; $R_3$ is hydrogen; $R_4$ is $C_1$-$C_6$ alkyl; $R_6$ is hydrogen; $Q_2$ is CH; $Q_3$ is CH; $Q_4$ is N; and Y is O; then Z is selected from the group consisting of:

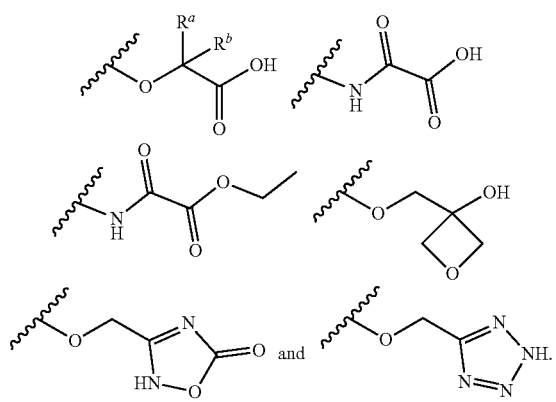

In another aspect, disclosed herein are compounds of Formula I:

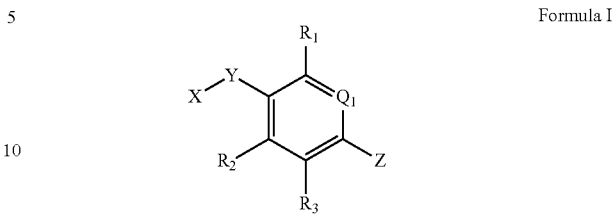

Formula I or a stereoisomer or a tautomer thereof, or a pharmaceutically acceptable salt thereof, wherein $Q_1$ is CH or N;

$R_1$ and $R_2$ are each independently selected from hydrogen, halogen, cyclopropyl, and $C_{1-3}$ alkyl optionally substituted with 1 to 5 fluorine;

$R_3$ is selected from hydrogen, deuterium, halogen, —CN, alkoxy, and $C_{1-6}$ alkyl; or $R_2$ and $R_3$ taken together along with the carbon atoms to which they are attached form a 4- to 6-membered carbocyclic ring or a four- to six-membered heterocyclic ring;

X is an optionally substituted 6- to 10-membered heterocycle;

Y is O or $CH_2$;

Z is selected from the group consisting of:

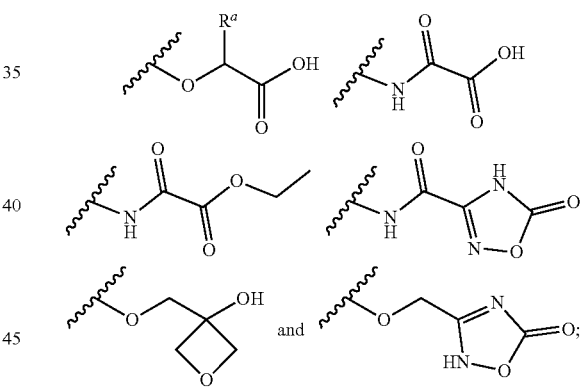

and $R^a$ is selected from hydrogen, methyl, and fluorine.

In some embodiments, X is:

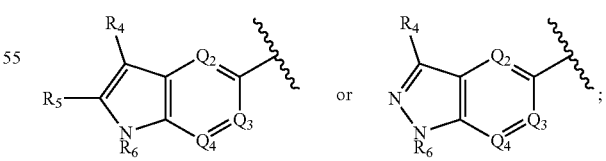

wherein $R_4$ is selected from hydrogen; $C_1$-$C_6$ alkyl; a non-aromatic $C_3$-$C_{12}$ carbocyclic ring; a $C_6$-$C_{10}$ aryl group; a (carbocyclic)alkyl group; and an aralkyl group; and $R_4$ is optionally substituted with one to three $R_k$ independently selected from halogen, —CN, $C_1$-$C_6$ alkyl, $C_1$-$C_6$ alkoxy, $C_1$-$C_6$ haloalkyl, and $C_1$-$C_6$ haloalkoxy;

$R_5$ is selected from hydrogen; halogen; $C_1$-$C_6$ alkyl optionally substituted with halogen or $C_1$-$C_6$ alkoxy; and $C_3$-$C_9$ cycloalkyl optionally substituted with halogen or $C_1$-$C_6$ alkoxy;

$R_6$ is hydrogen or $C_1$-$C_3$ alkyl; and $Q_2$, $Q_3$, and $Q_4$ are each independently selected from CH or N, and at least one of $Q_2$, $Q_3$, and $Q_4$ must be N.

In some embodiments, X is

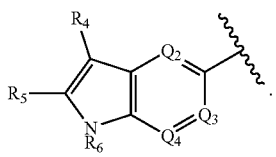

In some embodiments, X is

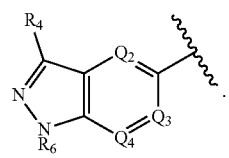

In some embodiments, X is:

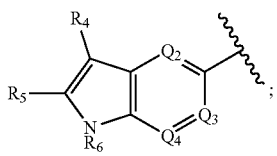

$R_4$ is selected from hydrogen; $C_1$-$C_6$ alkyl; a non-aromatic $C_3$-$C_{12}$ carbocyclic ring; a $C_6$-$C_{10}$ aryl group; a (carbocyclic)alkyl group; and an aralkyl group; wherein $R_4$ is optionally substituted with one to three $R_k$ independently selected from halogen, —CN, $C_1$-$C_6$ alkyl, $C_1$-$C_6$ alkoxy, $C_1$-$C_6$ haloalkyl, and $C_1$-$C_6$ haloalkoxy;

$R_5$ is selected from hydrogen; halogen; $C_1$-$C_6$ alkyl optionally substituted with halogen or $C_1$-$C_6$ alkoxy; and $C_3$-$C_9$ cycloalkyl optionally substituted with halogen or $C_1$-$C_6$ alkoxy;

$R_6$ is hydrogen or $C_1$-$C_3$ alkyl; and $Q_2$, $Q_3$, and $Q_4$ are each independently selected from CH or N, and at least one of $Q_2$, $Q_3$, and $Q_4$ must be N.

In some embodiments, X is:

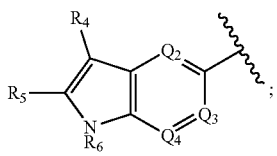

$R_4$ and $R_5$ taken together along with the carbon atoms to which they are attached form a 4- to 6-membered carbocyclic ring;

$R_6$ is hydrogen or $C_1$-$C_3$ alkyl; and $Q_2$, $Q_3$, and $Q_4$ are each independently selected from CH or N, and at least one of $Q_2$, $Q_3$, and $Q_4$ must be N.

In some embodiments, $R_4$ is hydrogen. In some embodiments, $R_4$ is $C_1$-$C_6$ alkyl. In some embodiments, $R_4$ is isopropyl. In some embodiments, $R_4$ is a non-aromatic $C_3$-$C_{12}$ carbocyclic ring. In some embodiments, $R_4$ is a $C_6$-$C_{10}$ aryl group. In some embodiments, $R_4$ is a (carbocyclic)alkyl group. In some embodiments, $R_4$ is an aralkyl group.

In some embodiments, $R_5$ is hydrogen. In some embodiments, $R_5$ is halogen. In some embodiments, $R_5$ is $C_1$-$C_6$ alkyl optionally substituted with halogen or $C_1$-$C_6$ alkoxy. In some embodiments, $R_5$ is $C_1$-$C_6$ alkyl. In some embodiments, $R_5$ is $C_3$-$C_9$ cycloalkyl optionally substituted with halogen or $C_1$-$C_6$ alkoxy. In some embodiments, $R_5$ is $C_3$-$C_9$ cycloalkyl.

In some embodiments, $R_4$ and $R_5$ taken together along with the carbon atoms to which they are attached form a 4- to 6-membered carbocyclic ring. In some embodiments, $R_4$ and $R_5$ taken together along with the carbon atoms to which they are attached form a 4-membered carbocyclic ring. In some embodiments, $R_4$ and $R_5$ taken together along with the carbon atoms to which they are attached form a 5-membered carbocyclic ring. In some embodiments, $R_4$ and $R_5$ taken together along with the carbon atoms to which they are attached form a 6-membered carbocyclic ring.

In some embodiments, $R_6$ is hydrogen. In some embodiments, $R_6$ is $C_1$-$C_3$ alkyl.

In some embodiments, $Q_2$ is N.
In some embodiments, $Q_3$ is N.
In some embodiments, $Q_4$ is N.
In some embodiments, $Q_3$ and $Q_4$ are CH.
In some embodiments, $Q_2$ is N, and $Q_3$ and $Q_4$ are CH.
In some embodiments, $Q_3$ is N, and $Q_2$ and $Q_4$ are CH.
In some embodiments, $Q_4$ is N, and $Q_2$ and $Q_3$ are CH.

In some embodiments, the compound has the chemical structure of Formula I'a:

Formula I'a

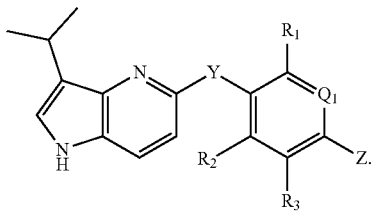

In some embodiments, Y is $CH_2$. In some embodiments, Y is O.

In some embodiments, $R_1$ and $R_2$ are each independently selected from halogen, cyclopropyl, and $C_{1-3}$ alkyl optionally substituted with 1 to 5 fluorine.

In some embodiments, $R_1$ is hydrogen. In some embodiments, $R_1$ is halogen. In some embodiments, $R_1$ is cyclopropyl. In some embodiments, $R_1$ is $C_{1-3}$ alkyl optionally substituted with 1 to 5 fluorine. In some embodiments, $R_1$ is $C_{1-3}$ alkyl.

In some embodiments, $R_2$ is hydrogen. In some embodiments, $R_2$ is halogen. In some embodiments, $R_2$ is cyclopropyl. In some embodiments, $R_2$ is $C_{1-3}$ alkyl optionally substituted with 1 to 5 fluorine. In some embodiments, $R_2$ is $C_{1-3}$ alkyl.

In some embodiments, $R_1$ and $R_2$ are each independently $C_{1-3}$ alkyl. In some embodiments, $R_1$ and $R_2$ are both $CH_3$.

In some embodiments, $R_3$ is hydrogen. In some embodiments, $R_3$ is deuterium. In some embodiments, $R_3$ is halogen. In some embodiments, $R_3$ is —CN. In some embodiments, $R_3$ is $C_{1-10}$ alkoxy. In some embodiments, $R_3$ is $C_{1-6}$ alkyl. In some embodiments, $R_3$ is $CH_3$. In some embodiments, $R_3$ is hydrogen or $CH_3$.

In some embodiments, $R_1$, $R_2$, and $R_3$ are each independently $C_{1-3}$ alkyl. In some embodiments, $R_1$, $R_2$, and $R_3$ are $CH_3$.

In some embodiments, $R_2$ and $R_3$ taken together along with the carbon atoms to which they are attached form a 4- to 6-membered carbocyclic ring or a four- to six-membered heterocyclic ring. In some embodiments, $R_2$ and $R_3$ taken together along with the carbon atoms to which they are attached form a 4-membered carbocyclic ring or a four- to six-membered heterocyclic ring. In some embodiments, $R_2$ and $R_3$ taken together along with the carbon atoms to which they are attached form a 5-membered carbocyclic ring or a four- to six-membered heterocyclic ring. In some embodiments, $R_2$ and $R_3$ taken together along with the carbon atoms to which they are attached form a 6-membered carbocyclic ring or a four- to six-membered heterocyclic ring.

In some embodiments, $Q_1$ is CH. In some embodiments, $Q_1$ is N.

In some embodiments, Z is selected from the group consisting of:

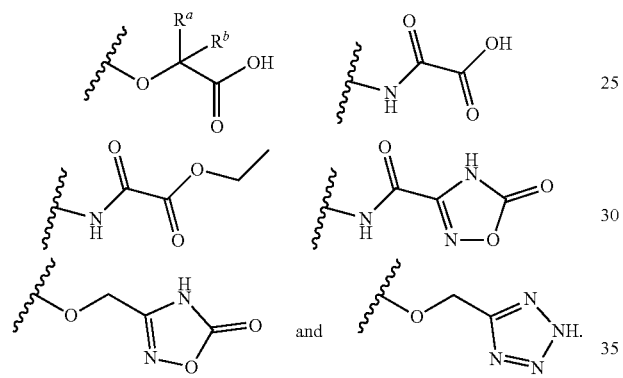

In some embodiments, Z is selected from the group consisting of:

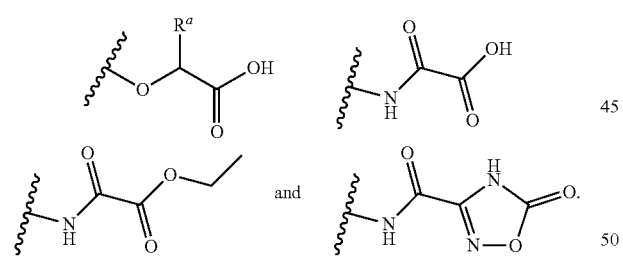

In some embodiments, Z is selected from the group consisting of:

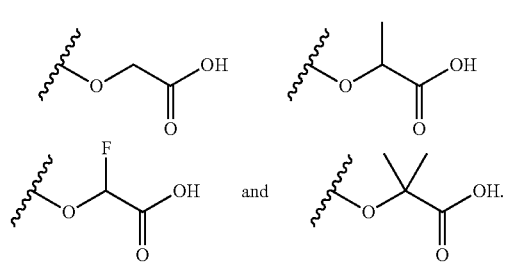

In some embodiments, Z is

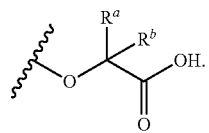

In some embodiments, Z is

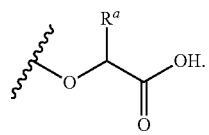

In some embodiments, Z is

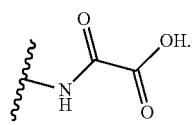 [SMILES: *NC(=O)C(=O)O]

In some embodiments, Z is

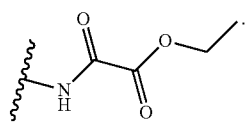 [SMILES: *NC(=O)C(=O)OCC]

In some embodiments, Z is

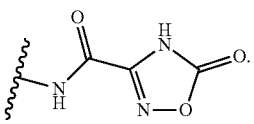 [SMILES: *NC(=O)c1noc(=O)[nH]1]

In some embodiments, Z is

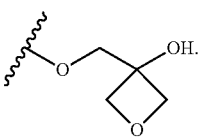 [SMILES: *OCC1(O)COC1]

In some embodiments, Z is

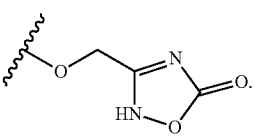 [SMILES: *OCc1nc(=O)o[nH]1]

In some embodiments, Z is

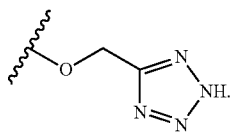 [SMILES: *OCc1nn[nH]n1]

In some embodiments, Z is

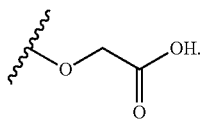 [SMILES: *OCC(=O)O]

In some embodiments, Z is

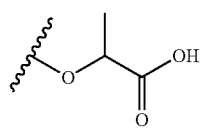 [SMILES: *OC(C)C(=O)O]

In some embodiments, Z is

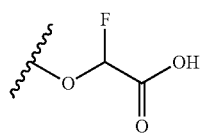 [SMILES: *OC(F)C(=O)O]

In some embodiments, Z is

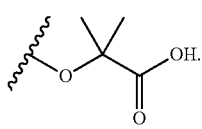 [SMILES: *OC(C)(C)C(=O)O]

In some embodiments, $R^a$ is hydrogen. In some embodiments, $R^a$ is methyl. In some embodiments, $R^a$ is fluorine.

In another aspect, disclosed herein is a compound selected from the group consisting of:
2-(4-((3-isopropyl-1H-pyrrolo[3,2-b]pyridin-5-yl)methyl)-2,3,5-trimethylphenoxy)acetic acid;
2-(4-((3-isopropyl-1H-pyrrolo[3,2-b]pyridin-5-yl)methyl)-3,5-dimethylphenoxy)acetic acid;
N-(4-((3-isopropyl-1H-pyrrolo[3,2-b]pyridin-5-yl)methyl)-3,5-dimethylphenyl)-5-oxo-4,5-dihydro-1,2,4-oxadiazole-3-carboxamide;
2-((4((3-isopropyl-1H-pyrrolo[3,2-b]pyridin-5-yl)methyl)-3,5-dimethylphenyl)amino)-2-oxoacetic acid; and
ethyl 2-((4-((3-isopropyl-1H-pyrrolo[3,2-b]pyridin-5-yl)methyl)-3,5-dimethylphenyl)amino)-2-oxoacetate;
[[5-([3-isopropyl-1H-pyrrolo[3,2-b]pyridin-5-yl]methyl)-3,4,6-trimethylpyridin-2-yl]oxy]acetic acid;
4-[[3-isopropyl-1-(4-methylbenzenesulfonyl)pyrrolo[3,2-b]pyridin-5-yl]methyl]-2,3,5-trimethylphenol;
2-(4-((3-isopropyl-1H-pyrrolo[3,2-b]pyridin-5-yl)methyl)-2,3,5-trimethylphenoxy)propanoic acid;
2-(4-((3-isopropyl-1H-pyrrolo[3,2-b]pyridin-5-yl)methyl)-2,3,5-trimethylphenoxy)-2-methylpropanoic acid;
2-fluoro-2-(4-((3-isopropyl-1H-pyrrolo[3,2-b]pyridin-5-yl)methyl)-2,3,5-trimethylphenoxy)acetic acid;
5-(4-((2H-tetrazol-5-yl)methoxy)-2,3,6-trimethylbenzyl)-3-isopropyl-1H-pyrrolo[3,2-b]pyridine; and
3-((4-((3-isopropyl-1H-pyrrolo[3,2-b]pyridin-5-yl)methyl)-2,3,5-trimethylphenoxy)methyl)-1,2,4-oxadiazol-5(4H)-one;
or a stereoisomer or a tautomer thereof, or a pharmaceutically acceptable salt thereof.

In another aspect, disclosed herein is a compound selected from the group consisting of:
2-(4-((3-isopropyl-1H-pyrrolo[3,2-b]pyridin-5-yl)methyl)-2,3,5-trimethylphenoxy)acetic acid;
2-(4-((3-isopropyl-1H-pyrrolo[3,2-b]pyridin-5-yl)methyl)-3,5-dimethylphenoxy)acetic acid;
N-(4-((3-isopropyl-1H-pyrrolo[3,2-b]pyridin-5-yl)methyl)-3,5-dimethylphenyl)-5-oxo-4,5-dihydro-1,2,4-oxadiazole-3-carboxamide;
2-((4-((3-isopropyl-1H-pyrrolo[3,2-b]pyridin-5-yl)methyl)-3,5-dimethylphenyl)amino)-2-oxoacetic acid; and
ethyl 2-((4-((3-isopropyl-1H-pyrrolo[3,2-b]pyridin-5-yl)methyl)-3,5-dimethylphenyl)amino)-2-oxoacetate;
or a stereoisomer or a tautomer thereof, or a pharmaceutically acceptable salt thereof.

In another aspect, disclosed herein are as described herein, or a stereoisomer or a tautomer thereof, or a pharmaceutically acceptable salt thereof, for use in treating a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

In another aspect, disclosed herein are as described herein, or a stereoisomer or a tautomer thereof, or a pharmaceutically acceptable salt thereof, for use in selectively modulating the activity of a thyroid hormone receptor beta (THR-β).

Pharmaceutical Compositions

In another aspect, disclosed herein are pharmaceutical compositions comprising, consisting essentially of, or consisting of a compound as described herein, and at least one pharmaceutically acceptable excipient.

In another aspect, disclosed herein are pharmaceutical compositions comprising, consisting essentially of, or consisting of a compound of Formula I', as described herein, and at least one pharmaceutically acceptable excipient.

In another aspect, disclosed herein are pharmaceutical compositions comprising, consisting essentially of, or consisting of a compound of Formula I, as described herein, and at least one pharmaceutically acceptable excipient.

In another aspect, disclosed herein are pharmaceutical compositions comprising, consisting essentially of, or consisting of a compound as described herein, for use in treating a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

In another aspect, disclosed herein are pharmaceutical compositions comprising, consisting essentially of, or consisting of a compound as described herein, for use in selectively modulating the activity of a thyroid hormone receptor beta (THR-β).

The pharmaceutical composition disclosed herein may comprise a pharmaceutically acceptable carrier, such as diluents, disintegrants, sweetening agents, glidants, or flavoring agents and may be formulated into an oral dosage form such as tablets, capsules, powders, granules, suspensions, emulsions, or syrups; or a parenteral dosage form such as liquids for external use, suspensions for external use, emulsions for external use, gels (ointments or the like), inhaling agents, spraying agents, injections, etc. Said dosage forms may be formulated in various forms, e.g., a dosage form for single administration or for multiple administrations.

The pharmaceutical composition disclosed herein may include excipients such as lactose, corn starch, or the like, glidants such as magnesium stearate, etc., emulsifying agents, suspending agents, stabilizers, and isotonic agents, etc. If desired, a sweetening agent and/or a flavoring agent may be added. Exemplary excipients include, without limitation, polyethylene glycol (PEG), hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Inorganic salt or buffers include, but are not limited to, citric acid, sodium chloride, potassium chloride, sodium sulfate, potassium nitrate, sodium phosphate monobasic, sodium phosphate dibasic, and combinations thereof.

Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition disclosed herein may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Non-limiting examples of suitable bases include bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the role of the excipient, the dosage requirements of the active agent components, and particular needs of the composition. Generally, however, the excipient will be present in the composition in an amount of about 1% to about 99% by weight, preferably from about 5% to about 98% by weight, more preferably from about 15 to about 95% by weight of the excipient. In general, the amount of excipient present in a composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

The pharmaceutical compositions described herein can be administered to a human patient per se, or in pharmaceutical compositions where they are mixed with one or more other active ingredients, as in combination therapy, or suitable carriers or excipient(s). In some embodiments, the one or more other active ingredients comprises or consists of a KHK inhibitor. In some embodiments, the KHK inhibitor is PF-06835919. In some embodiments, the one or more other active ingredients comprises or consists of an FXR agonist. In some embodiments, the FXR agonist is TERN-101 (LY2562175). In some embodiments, the FXR agonist is Tropifexor. In some embodiments, the FXR agonist is obeticholic acid (OCA). In some embodiments, the FXR agonist is ASC42. In some embodiments, the one or more other active ingredients comprises or consists of an SSAO inhibitor. In some embodiments, the SSAO inhibitor is TERN-201. In some embodiments, the one or more other active ingredients comprises or consists of an FASN inhibitor. In some embodiments, the FASN inhibitor is ASC40. In some embodiments, the one or more other active ingredients comprises or consists of an SCD1 inhibitor. In some embodiments, the SCD1 inhibitor is aramchol.

Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, transdermal, rectal, transmucosal, or intestinal administration; parenteral delivery, including intramuscular, subcutaneous, intravenous, intramedullary injections, as well as inhalation, intrathecal, direct intraventricular, intraperitoneal, intranasal, or intraocular injections.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. These pharmaceutical compositions, then, may be formulated in a conventional manner using one or more known physiologically acceptable carriers comprising excipients and/or auxiliaries, which facilitate processing of the active compounds into preparations that can be used pharmaceutically. Any of the well-known techniques, carriers, and excipients may be used as suitable and as understood in the art; e.g., in Remington's Pharmaceutical Sciences, above.

Pharmaceutical compositions suitable for use in the presently disclosed formulations include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. In some embodiments, a therapeutically effective amount means an amount of compound effective to alleviate or ameliorate symptoms of disease or prolong the survival of the subject being treated.

Although the exact dosage can be determined on a drug-by-drug basis, in most cases, some generalizations regarding the dosage can be made. The daily dosage regimen for an adult human patient may be, for example, an oral dose of between 0.001 mg and 1000 mg of each ingredient, preferably between 0.01 mg and 500 mg, for example 1 to 200 mg or each active ingredient of the pharmaceutical compositions disclosed herein or a pharmaceutically acceptable salt thereof calculated as the free base or free acid, the composition being administered 1 to 4 times per day or per week. Alternatively, the compositions disclosed herein may be administered by continuous such as sustained, delayed, or extended release, preferably at a dose of each ingredient up to 500 mg per day. Thus, the total daily dosage by oral administration of each ingredient will typically be in the range 0.1 mg to 2000 mg.

Methods of Treatment

In another aspect, disclosed herein are methods of treating a thyroid hormone receptor related disorder in a patient, the method comprising, consisting essentially of, or consisting of the steps of identifying a patient in need of treatment for the thyroid hormone receptor related disorder, and administering to the patient, or contacting the patient with, a compound as described herein.

In another aspect, disclosed herein are methods of treating a thyroid hormone receptor related disorder in a patient, the method comprising, consisting essentially of, or consisting of the steps of identifying a patient in need of treatment for the thyroid hormone receptor related disorder, and administering to the patient, or contacting the patient with, a compound of Formula I, as described herein.

In some embodiments, a health care professional, such as a physician, physician's assistant, nurse practitioner, or the like, identifies an individual as being in need of treatment for the thyroid hormone receptor related disorder, and/or a candidate for treatment with a compound disclosed herein. The identification may be based on medical test results, non-responsiveness to other, first-line therapies, the specific nature of the particular liver disorder, or the like.

In some embodiments, the thyroid hormone receptor related disorder is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

In another aspect, disclosed herein are methods of treating a disorder or disease in a subject in need thereof, the method comprising, consisting essentially of, or consisting of administering to the subject a therapeutically effective amount of a compound or composition disclosed herein, wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer. In some embodiments, the compound or composition disclosed herein is administered in combination with a KHK inhibitor, an FXR agonist, a SSAO inhibitor, a FASN inhibitor, or a SCD1 modulator. In some embodiments, the KHK inhibitor is PF-06835919; the FXR agonist is TERN-101 (LY2562175), Tropifexor, obeticholic acid (OCA), or ASC42; the SSAO inhibitor is TERN-201; the FASN inhibitor is ASC40; and the SCD1 modulator is aramchol.

In another aspect, disclosed herein are methods of treating NASH in a subject in need thereof, the method comprising, consisting essentially of, or consisting of administering to the subject a therapeutically effective amount of a compound or composition disclosed herein.

In another aspect, disclosed herein are methods of treating obesity in a subject in need thereof, the method comprising, consisting essentially of, or consisting of administering to the subject a therapeutically effective amount of a compound or composition disclosed herein.

In another aspect, disclosed herein are methods of treating hyperlipidemia in a subject in need thereof, the method comprising, consisting essentially of, or consisting of administering to the subject a therapeutically effective amount of a compound or composition disclosed herein.

In another aspect, disclosed herein are methods of treating hypercholesterolemia in a subject in need thereof, the method comprising, consisting essentially of, or consisting of administering to the subject a therapeutically effective amount of a compound or composition disclosed herein.

In another aspect, disclosed herein are methods of treating diabetes in a subject in need thereof, the method comprising, consisting essentially of, or consisting of administering to the subject a therapeutically effective amount of a compound or composition disclosed herein.

In another aspect, disclosed herein are methods of treating liver steatosis in a subject in need thereof, the method comprising, consisting essentially of, or consisting of administering to the subject a therapeutically effective amount of a compound or composition disclosed herein.

In another aspect, disclosed herein are methods of selectively modulating the activity of a thyroid hormone receptor beta (THR-β) comprising, consisting essentially of, or consisting of contacting a compound as described herein, with a thyroid hormone receptor. In some embodiments, the contacting is in vitro or ex vivo, whereas in other embodiments, the contacting is in vivo.

In another aspect, disclosed herein are methods of selectively modulating the activity of a thyroid hormone receptor beta (THR-β) comprising, consisting essentially of, or consisting of contacting a compound of Formula I', as described herein, with a thyroid hormone receptor. In some embodiments, the contacting is in vitro or ex vivo, whereas in other embodiments, the contacting is in vivo.

In another aspect, disclosed herein are methods of selectively modulating the activity of a thyroid hormone receptor beta (THR-β) comprising, consisting essentially of, or consisting of contacting a compound of Formula I, as described herein, with a thyroid hormone receptor. In some embodiments, the contacting is in vitro or ex vivo, whereas in other embodiments, the contacting is in vivo.

In another aspect, disclosed herein are methods of selectively modulating the activity of a thyroid hormone receptor beta (THR-β) comprising, consisting essentially of, or consisting of contacting a composition described herein, with a thyroid hormone receptor. In some embodiments, the contacting is in vitro or ex vivo, whereas in other embodiments, the contacting is in vivo.

EXAMPLES

The following exemplify aspects of the present invention and is not limiting of its scope. Conditions for the preparation of several of the compounds disclosed herein are presented. Procedures for the synthesis of common intermediates are provided only once. The chemical names were generated using Marvin 17.28.0 or ChemDraw 18.1 or ChemBioDraw Ultra 13.0.

Table of Abbreviations:

The following abbreviations are used in the present disclosure:

| | |
|---|---|
| anhyd. | Anhydrous |
| aq. | Aqueous |
| Bu | Butyl |

| | |
|---|---|
| conc. | Concentrated |
| CyH | cyclohexane |
| DIPEA | N,N-Diisopropylethylamine |
| DMAP | 4-dimethylaminopyridine |
| DMF | N,N-Dimethylformamide |
| DMSO | Dimethyl sulfoxide |
| EA | Ethyl acetate |
| FA | Formic acid |
| h | Hour(s) |
| Me | Methyl |
| MEK | Methyl ethyl ketone |
| min | Minute(s) |
| PE | Petroleum ether |
| rt | Room temperature |
| Rt | Retention time |
| sat. | Saturated |
| TBAF | Tetra-n-butylammonium fluoride |
| TFA | Trifluoroacetic acid |
| THF | Tetrahydrofuran |

Synthesis of Compounds

Example 1

Synthesis of Compound 1: 2-(4-((3-isopropyl-1H-pyrrolo[3,2-b]pyridin-5-yl)methyl)-2,3,5-trimethylphenoxy)acetic acid.

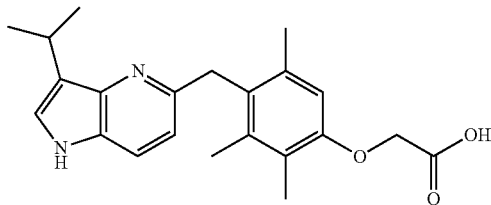 [SMILES: Cc1cc(OCC(=O)O)c(C)c(C)c1Cc1ccc2[nH]cc(C(C)C)c2n1]

A solution of NaNO$_2$ (1.99 g, 28.90 mmol) in water (20 mL) is added dropwise to a stirred solution of 6-bromopyridin-3-amine (5 g, 28.90 mmol) in HCl (6 M aq., 100 mL) at 0° C. The reaction mixture was stirred for 0.5 hour at 0° C. Then a solution of SnCl$_2$.2H$_2$O (16.30 g, 72.25 mmol) in HCl (6 M, 100 mL) is added to the reaction mixture at 0° C. and stirred for 0.5 hour. The reaction mixture is basified to pH 10 with KOH (1M, aq.), the solid was removed by filtration, and the aqueous layer is extracted with EA (3×100 mL). The organic layers are combined, dried over sodium sulfate and concentrated under vacuo to afford the crude product, which was purified by silica gel chromatography, (eluent : 0 to 100% EA/PE) to afford (6-bromo-3-pyridyl)hydrazine (3.3 g, 17.55 mmol, 61% yield) as a white solid.

To a solution of (6-bromo-3-pyridyl)hydrazine (6 g, 31.91 mmol) in ethanol (60 mL) was added dropwise 3-methylbutanal (3.30 g, 38.29 mmol, 4.20 mL) at 0° C. The mixture was stirred at 20° C. for 1 h. The mixture was concentrated under reduced pressure to give 6-bromo-N-[3-methylbutylideneamino]pyridin-3-amine (8.17 g, crude) as an orange red solid, which was used in the next step without further purification.

A mixture of 6-bromo-N-[3-methylbutylideneamino]pyridin-3-amine (8.17 g, 31.90 mmol) and ZnBr$_2$ (14.37 g, 63.79 mmol) was stirred at 160° C. for 1 h. The reaction mixture was diluted with H$_2$O (10 mL) and extracted with EA (20 mL×2). The combined organic layers were washed with brine (10 mL), dried over anhydrous Na$_2$SO$_4$, filtered and concentrated under reduced pressure to give a residue, which was purified by silica gel chromatography, (eluent : 0 to 30% EA/PE) to give a mixture of 5-chloro-3-isopropyl-1H-pyrrolo[3,2-b]pyridine and 5-bromo-3-isopropyl-1H-pyrrolo[3,2-b]pyridine (4.0 g) as a yellow solid. $^1$H NMR (400 MHz, CDCl$_3$) δ 8.71-8.37 (m, 1H), 7.59 (d, J=8.5 Hz, 1H), 7.50 (d, J=8.5 Hz, 1H), 7.53-7.48 (m, 1H), 7.26-7.19 (m, 1H), 7.10 (s, 1H), 3.38 (td, J=6.9, 13.8 Hz, 1H), 1.37-1.36 (m, 3H).

A mixture of 5-bromo-3-isopropyl-1H-pyrrolo[3,2-b]pyridine (2.66 g, 11.11 mmol), 4-methylbenzenesulfonyl chloride (4.24 g, 22.22 mmol), DMAP (27.14 mg, 0.222 mmol) and DIPEA (3.16 g, 24.44 mmol, 4.26 mL) in CH$_2$Cl$_2$ (150 mL) was stirred at 25° C. for 12 h under N$_2$. The mixture reaction was concentrated under reduced pressure. The crude product was purified by silica gel chromatography (EA/PE=0~10%) to give 5-bromo-3-isopropyl-1-(p-tolylsulfonyl)pyrrolo-[3,2-b]pyridine (2.60 g, 6.45 mmol, 58% yield, 97% purity) as a yellow solid. $^1$H NMR (400 MHz, CDCl$_3$) δ 8.08 (d, J=8.6 Hz, 1H), 7.76-7.68 (m, 2H), 7.51-7.46 (m, 1H), 7.37-7.37 (m, 1H), 7.36 (d, J=8.6 Hz, 1H), 7.38-7.33 (m, 1H), 7.27 (s, 2H), 3.33-3.19 (m, 1H), 2.38 (s, 3H), 1.33 (d, J=6.8 Hz, 6H). LC-MS Method A, Rt: 1.615, (ESI, m/z): 395[M+H]$^+$.

A mixture of 4-bromo-2,3,5-trimethyl-phenol (16.6 g, 77.18 mmol), BnBr (13.86 g, 81.04 mmol, 9.63 mL) and K$_2$CO$_3$ (32 g, 231.53 mmol) in CH$_3$CN (200 mL) was stirred at 20° C. for 20 hrs. The mixture was diluted with EA (500 mL) and washed with H$_2$O (3×200 mL). The organic layer was dried over anhydrous MgSO$_4$, the solids were removed by filtration, and the filtrate was concentrated to give crude product, which was purified by silica gel chromatography (EA in PE=0~2%) to afford 1-benzyloxy-4-bromo-2,3,5-trimethyl-benzene (22.76 g, 74.57 mmol, 97% yield) as a white solid. $^1$H NMR (400 MHz, CDCl$_3$) δ 7.38-7.24 (m, 5H), 6.64 (s, 1H), 4.96 (s, 2H), 2.32 (d, J=9.9 Hz, 6H), 2.18 (s, 3H), 1.49 (s, 1H).

A mixture of 1-(benzyloxy)-4-bromo-2,3,5-trimethylbenzene (1.8 g, 5.90 mmol), bis(4,4,5,5-tetramethyl-1,3,2-dioxaborolan-2-yl)methane (3.16 g, 11.80 mmol) and Pd[P(t-Bu)$_3$]$_2$ (301.40 mg, 0.590 mmol) in dioxane (60 mL) was degassed and purged thrice with N$_2$, followed by addition of KOH (8 M, 1.47 mL). After the addition, the mixture was stirred at 30° C. for 12 h under N$_2$. The reaction mixture was diluted with H$_2$O (40 mL) and extracted with EA (3×50 mL). The combined organic layers were washed with brine (2×100 mL), dried over NaSO$_4$, the solids were removed by filtration and the filtrate was concentrated under reduced pressure. The crude product was purified by silica gel chromatography (EA in PE=0~3%) to afford 2-(4-(benzyloxy)-2,3,6-trimethylbenzyl)-4,4,5,5-tetramethyl-1,3,2-dioxaborolane (1.77 g, 4.79 mmol, 81% yield, 99% purity) as a brown solid. $^1$H NMR (400 MHz, CDCl$_3$) δ 7.51-7.46 (m, 2H), 7.44-7.37 (m, 2H), 7.37-7.30 (m, 1H), 6.66 (s, 1H), 5.03 (s, 2H), 2.28 (s, 3H), 2.24 (s, 5H), 2.22 (s, 3H), 1.24 (s, 12H). LC-MS Method B, Rt: 1.169, (ESI, m/z): 367[M+H]$^+$.

The mixture of 5-bromo-3 sopropyl-1-(p-tolylsulfonyl) pyrrolo[3,2-b]pyridine (536.85 mg, 1.37 mmol), 2-[(4-benzyloxy-2,3,6-trimethyl-phenyl)methyl]-4,4,5,5-tetramethyl-1,3,2-dioxaborolane (1 g, 2.73 mmol), PdCl$_2$[P(o-Tol)$_3$]$_2$ (160.95 mg, 0.205 mmol) and K$_3$PO$_4$ (869.23 mg, 4.10 mmol) in dioxane (60 mL) and H$_2$O (6 mL) was stirred at 100° C. for 24 h under N$_2$. The reaction mixture was diluted with H$_2$O (50 mL) and extracted with EA (50 mL×4). The combined organic layers were dried over Na$_2$SO$_4$, the solids were removed by filtration and the filtrate was concentrated under reduced pressure. The crude product was purified by preparatory silica TLC, PE: EA=5:1, to afford 5-[(4-benzyloxy-2,3,6-trimethyl-phenyl)methyl]-3-isopropyl-1-(p- tolylsulfonyl)pyrrolo [3,2-b] pyridine (476 mg, 63% yield) as a yellow solid. LC-MS Method A, Rt: 1.624, (ESI, m/z): 553[M+H]+.

To a solution of 5-[(4-benzyloxy-2,3,6-trimethyl-phenyl) methyl]-3-isopropyl-1-(p-tolylsulfonyl) pyrrolo[3,2-b]pyridine (600 mg, 1.09 mmol) in $CH_2Cl_2$ (20 mL) was added $BBr_3$ (1.36 g, 5.43 mmol, 0.523 mL) at 0° C. under $N_2$. The mixture was stirred at 0° C. for 2 h under $N_2$. The reaction mixture was quenched by addition of saturated aq. $NaHCO_3$ (10 mL) at 0° C., and then diluted with $H_2O$ (20 mL) and extracted with $CH_2Cl_2$ (4×30 mL). The combined organic layers were dried over $Na_2SO_4$, the solids were removed by filtration and the filtrate was concentrated under reduced pressure. The crude product was purified by silica gel chromatography (eluent: 0 to 20% EA/PE) to afford 4-[[3-isopropyl-1-(mtolylsulfonyl)pyrrolo[3,2-b]pyridine-5-yl] methyl]-2,3,5-trimethyl-phenol (424 mg, 84% yield, 99% purity) as a white solid. $^1$H NMR (400 MHz, $CDCl_3$) δ 7.98 (d, J=8.5 Hz, 1H), 7.71 (d, J=8.4 Hz, 2H), 7.45 (d, J=1.0 Hz, 1H), 7.22 (d, J=8.1 Hz, 2H), 6.68 (d, J=8.6 Hz, 1H), 6.56 (s, 1H), 4.58 (s, 1H), 4.25 (s, 2H), 3.36-3.25 (m, 1H), 2.36 (s, 3H), 2.23 (s, 3H), 2.17 (d, J=6.1 Hz, 6H), 2.06 (s, 1H), 1.36 (d, J=6.9 Hz, 6H). LC-MS Method B, Rt: 1.016, (ESI, m/z): 463[M+H]+.

NaOH (185.47 mg, 4.64 mmol) was added to a solution of 4-[[3-isopropyl-1-(p-tolylsulfonyl)pyrrolo[3,2-b]pyridin-5-yl]methyl]-2,3,5-trimethyl-phenol (390 mg, 0.843 mmol) in MEK (20 mL) at 20° C. After the addition, the mixture was stirred at 50° C. for 1 h, followed by addition of a solution of 2-bromoacetic acid (140.57 mg, 1.01 mmol, 0.073 mL) in MEK (2 mL). Then the mixture was stirred at 50° C. for 4 h. The reaction mixture was diluted with $H_2O$ (15 mL), acidified with HCl (1M, aq.) to pH=2-3 and extracted with $CH_2Cl_2$ (3×20 mL). The combined organic layers were dried over $Na_2SO_4$, filtered and concentrated under reduced pressure to give crude 2-[4-[[3-isopropyl-1-(p-tolylsulfonyl)pyrrolo[3,2-b]pyridin-5-yl]methyl]-2,3,5-trimethyl-phenoxy]acetic acid (415 mg, crude) as a yellow solid, which was used into the next step without further purification. LC-MS Method A, Rt: 1.337, (ESI, m/z): 521 [M+H]+.

To a solution of 2-[4-[[3-isopropyl-1-(p-tolylsulfonyl) pyrrolo[3,2-b]pyridin-5-yl]methyl]-2,3,5-trimethyl-phenoxy]acetic acid (200 mg, 0.384 mmol) in THF (8 mL) was added TBAF (1 M, 3.84 mL) at 20° C. After the addition, the reaction mixture was stirred at 65° C. for 6 h under $N_2$. The reaction mixture was diluted with saturated aq. $NH_4Cl$ (20 mL) and extracted with EA (3×15 mL). The combined organic layers were dried over $Na_2SO_4$, the solids were removed by filtration and the filtrate was concentrated under reduced pressure. The crude product was purified by preparatory HPLC (FA conditions) to afford 2-[4-[(3-isopropyl-1H-pyrrolo[3,2-b]pyridin-5-yl)methyl]-2,3,5-trimethyl-phenoxy]acetic acid (27.61 mg, 20% yield, 99% purity) as a white solid. $^1$H NMR (400 MHz, DMSO-$d_6$) δ 10.79 (br s, 1H), 7.51 (br d, J=8.6 Hz, 1H), 7.28 (br s, 1H), 6.58 (s, 1H), 6.53 (d, J=8.4 Hz, 1H), 4.63 (s, 2H), 4.15 (s, 2H), 3.26-3.17 (m, 1H), 2.27 (s, 3H), 2.16 (s, 3H), 2.10 (s, 3H), 1.33 (d, J=6.9 Hz, 6H). LC-MS Method A, Rt: 0.985, (ESI, m/z): 367 [M+H]+.

Example 2

Synthesis of Compound 2: 2-(4-((3-isopropyl-1H-pyrrolo[3,2-b]pyridin-5-yl)methyl)-3,5-dimethylphenoxy)acetic acid

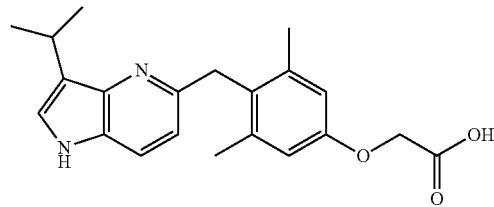 [SMILES: Cc1cc(OCC(=O)O)cc(C)c1Cc1ccc2[nH]cc(C(C)C)c2n1]

A mixture of 5-bromo-3-isopropyl-1-(p-tolylsulfonyl) pyrrolo[3,2-b]pyridine (502.40 mg, 1.28 mmol), 2-[(4-benzyloxy-2,6-dimethyl-phenyl)methyl]-4,4,5,5-tetramethyl-1, 3,2-dioxaborolane (900 mg, 2.55 mmol), $PdCl_2[P(o\text{-}Tol)_3]_2$ (150.62 mg, 0.192 mmol) and $K_3PO_4$ (813.46 mg, 3.83 mmol) in dioxane (30 mL) and $H_2O$ (3 mL) was stirred at 100° C. for 12 h under $N_2$. The reaction mixture was diluted with $H_2O$ (50 mL) and extracted with EA (4×50 mL). The combined organic layers were dried over $Na_2SO_4$, the solids were removed by filtration and the filtrate was concentrated under reduced pressure. The crude product was purified by silica gel chromatography (EA in PE=0-10%) to give 5-[(4-benzyloxy-2,6-dimethyl-phenyl)methyl]-3-isopropyl-1-(p-tolylsulfonyl)pyrrolo[3,2-b] pyridine (595 mg, 0.881 mmol, 69% yield, 80% purity) as a yellow solid. LC-MS Method B, Rt: 1.183, (ESI, m/z): 539[M+H]+.

To a solution of 5-[(4-benzyloxy-2,6-dimethyl-phenyl) methyl]-3-isopropyl-1-(p-tolylsulfonyl) pyrrolo[3,2-b]pyridine (490 mg, 0.910 mmol) in $CH_2Cl_2$ (20 mL) was added $BBr_3$ (1.14 g, 4.55 mmol) at 0° C. under $N_2$ and stirred at 0° C. for 2 h under $N_2$. The reaction mixture was quenched by addition of $NaHCO_3$ (10 mL, sat. aq.) at 0° C., then diluted with $H_2O$ (20 mL) and extracted with $CH_2Cl_2$ (4×30 mL). The combined organic layers were dried over $Na_2SO_4$, the solids were removed by filtration and the filtrate was concentrated under reduced pressure to give a residue. The residue was purified by silica gel chromatography (EA in PE=0~20%) to give 4-[[3-isopropyl-1-(p-tolylsulfonyl)pyrrolo[3,2-b]pyridin-5-yl]methyl]-3,5-dimethyl-phenol (289 mg, 0.623 mmol, 69% yield, 97% purity) as a yellow solid. $^1$H NMR (400 MHz, $CDCl_3$) δ 8.00 (d, J=8.5 Hz, 1H), 7.71 (d, J=8.4 Hz, 2H), 7.46 (d, J=0.9 Hz, 1H), 7.23 (d, J=8.0 Hz, 2H), 6.70 (d, J=8.5 Hz, 1H), 6.57 (s, 2H), 5.31 (s, 1H), 4.88 (s, 1H), 4.20 (s, 2H), 3.37-3.22 (m, 1H), 2.36 (s, 3H), 2.22 (s, 6H), 1.35 (d, J=6.9 Hz, 6H). LC-MS Method B, Rt: 0.983, (ESI, m/z): 449[M+H]+.

NaOH (58.85 mg, 1.47 mmol) was added to a solution of 4-[[3-isopropyl-1-(p-tolylsulfonyl)pyrrolo[3,2-b]pyridin-5-yl]methyl]-3,5-dimethyl-phenol (120 mg, 0.268 mmol) in MEK (5 mL) at 20° C. After the addition, the mixture was stirred at 50° C. for 1 h, followed by addition of a solution of 2-bromoacetic acid (44.60 mg, 0.321 mmol) in MEK (1.5 mL). Then the mixture solution was stirred at 50° C. for 4 h. The reaction mixture was diluted with $H_2O$ (15 mL), acidified with 1M aq. HCl to pH=2-3 and extracted with $CH_2Cl_2$ (3×20 mL). The combined organic layers were dried over $Na_2SO_4$, the solids were removed by filtration and the filtrate was concentrated under reduced pressure. The crude product was purified by preparatory silica TLC (PE: EA=2:

1) to give 2-[4-[[3-isopropyl-1-(mtolylsulfonyl)pyrrolo[3,2-b]pyridine-5-yl] methyl]-3,5-dimethyl-phenoxy]acetic acid (70 mg, 0.127 mmol, 47% yield, 92% purity) as a yellow solid. $^1$H NMR (400 MHz, CDCl$_3$) δ 8.03 (br d, J=8.6 Hz, 1H), 7.68 (d, J=8.3 Hz, 2H), 7.54-7.42 (m, 1H), 7.22 (br d, J=7.8 Hz, 2H), 6.72-6.57 (m, 3H), 4.70 (br s, 2H), 3.93 (s, 2H), 3.41-3.24 (m, 1H), 2.35 (s, 3H), 1.91-1.87 (m, 1H), 1.97 (s, 8H), 1.37-1.31 (m, 1H), 1.36 (br s, 1H), 1.38-1.17 (m, 9H), 1.30-1.17 (m, 1H).

To a solution of 2-[4-[[3-isopropyl-1-(p-tolylsulfonyl)pyrrolo[3,2-b]pyridin-5-yl]methyl]-3,5-dimethyl-phenoxy] acetic acid (140 mg, 0.276 mmol) in THF (10 mL) was added TBAF (1M in THF, 5.53 mL) at 20° C. After the addition, the mixture was stirred at 65° C. for 6 h under N$_2$. The reaction mixture was diluted with saturated aq. NH$_4$Cl (20 mL), extracted with EA (3×15 mL). The combined organic layers were dried over Na$_2$SO$_4$, the solids were removed by filtration and the filtrate was concentrated under reduced pressure. The crude product was purified by prep-HPLC (FA condition) to afford 2-[4-[(3-isopropyl-1H-pyrrolo[3,2-b]pyridin-5-yl)methyl]-3,5-dimethyl-phenoxy]acetic acid (20 mg, 0.056 mmol, 20% yield, 99% purity) as a white solid. $^1$H NMR (400 MHz, DMSO-d$_6$) δ 10.78 (br s, 1H), 8.15 (s, 1H), 7.51(d, J=8.4 Hz, 1H), 7.27 (d, J=2.1 Hz, 1H), 6.62-6.54 (m, 3H), 4.58 (s, 2H), 4.10 (s, 2H), 3.20 (td, J=6.8, 13.4 Hz, 1H), 2.27 (s, 6H), 1.32 (d, J=6.9 Hz, 6H). LC-MS Method A, Rt: 0.897, (ESI, m/z): 353 [M+H]$^+$.

Example 3

Synthesis of Compound 3: N-(4-((3-isopropyl-1H-pyrrolo[3,2-b]pyridin-5-yl)methyl)-3,5-dimethylphenyl)-5-oxo-4,5-dihydro-1,2,4-oxadiazole-3-carboxamide

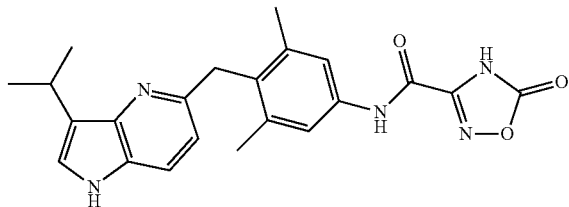 [SMILES: Cc1cc(NC(=O)c2noc(=O)[nH]2)cc(C)c1Cc1ccc2[nH]cc(C(C)C)c2n1]

To a solution of 4-[[3-isopropyl-1-(p-tolylsulfonyl)pyrrolo[3,2-b]pyridin-5-yl]methyl]-3,5-dimethyl-phenol (1 g, 2.23 mmol) and pyridine (440.84 mg, 5.57 mmol) in CH$_2$Cl$_2$ (25 mL) at 0° C. was added dropwise Tf$_2$O (754.76 mg, 2.68 mmol, 441.38 uL) slowly. After the addition, the mixture was stirred at 0° C. for 1 h. The reaction mixture was partitioned between H$_2$O (30 mL) and CH$_2$Cl$_2$ (30 mL). The organic phase was separated, washed with brine (3×10 mL), dried over anhydrous MgSO$_4$, the solids were removed by filtration and the filtrate was concentrated under reduced pressure to afford crude product, which was purified by silica gel chromatography (0~10% EA in PE) to give [4-[[3-isopropyl-1-(p-tolylsulfonyl)pyrrolo[3,2-b]pyridin-5-yl]methyl]-3,5-dimethyl-phenyl] trifluoromethanesulfonate (1.25 g, 2.15 mmol, 97% yield) as a colorless semisolid. $^1$H NMR (400 MHz, CDCl$_3$) δ 8.05 (d, J=8.5 Hz, 1H), 7.74 (d, J=8.4 Hz, 2H), 7.47 (d, J=0.8 Hz, 1H), 7.25 (d, J=8.3 Hz, 2H), 6.98 (s, 2H), 6.77 (d, J=8.5 Hz, 1H), 4.27 (s, 2H), 3.29-3.15 (m, 1H), 2.38 (s, 3H), 2.35 (s, 6H), 1.33 (d, J=6.9 Hz, 6H).

To a solution of [4-[[3-isopropyl-1-(mtolylsulfonyl)pyrrolo[3,2-b]pyridin-5-yl]methyl]-3,5-dimethyl-phenyl] trifluoromethanesulfonate (300 mg, 0.517 mmol) and t-butyl carbamate (121.05 mg, 1.03 mmol) in dioxane (8 mL) was added Pd$_2$(dba)$_3$ (47.31 mg, 0.052 mmol), (5-diphenylphosphanyl-9,9-dimethyl-xanthen-4-yl)-diphenyl-phosphane (59.79 mg, 0.103 mmol) and Cs$_2$CO$_3$ (505.03 mg, 1.55 mmol) at 20° C. under N$_2$ protection. Then the resulting mixture was stirred at 100° C. for 15 h under N$_2$. The mixture was diluted with H$_2$O (50 mL) and extracted with EA (3×50 mL). The combined organic layers were washed with brine (100 mL), dried over anhydrous Na$_2$SO$_4$, the solids were removed by filtration and the filtrate was concentrated under reduced pressure. The crude product was purified by silica gel chromatography (EA in PE=0~10%) to give t-butyl N-[4-[[3-isopropyl-1-(p-tolylsulfonyl)pyrrolo[3,2-b]pyridin-5-yl]methyl]-3,5-dimethyl-phenyl] carbamate (200 mg, 0.350 mmol, 68% yield, 96% purity) as a light yellow solid. $^1$H NMR (400 MHz, CDCl$_3$) δ 7.90 (d, J=8.5 Hz, 1H), 7.62 (d, J=8.4 Hz, 2H), 7.37 (s, 1H), 7.14 (d, J=8.1 Hz, 2H), 7.01 (s, 2H), 6.61 (d, J=8.6 Hz, 1H), 6.29 (s, 1H), 4.14 (s, 2H), 3.21(td, J=6.8, 13.5 Hz, 1H), 2.28 (s, 3H), 2.17 (s, 6H), 1.45 (s, 9H), 1.27 (d, J=6.9 Hz, 6H). LC-MS Method B, Rt: 1.440, (ESI, m/z): 548[M+H]$^+$.

To a solution of t-butyl N-[4-[[3-isopropyl-1-(p-tolylsulfonyl)pyrrolo[3,2-b]pyridin-5-yl]methyl]-3,5-dimethyl-phenyl] carbamate (170 mg, 0.310 mmol) in CH$_3$OH (3 mL) was added 4 M HCl in CH$_3$OH (8 mL) at 20° C. Then the resulting mixture was stirred at 20° C. for 12 h. CH$_3$OH was removed under reduced pressure and the residue was partitioned between EA (50 mL) and H$_2$O (50 mL). The EA phase was washed with H$_2$O (50 mL) again. The combined aqueous layers were adjusted to pH 7~8 with NaHCO$_3$ (sat. aq.), then extracted with EA (2×50 mL). The combined organic layers were washed with brine (50 mL), dried over anhydrous Na$_2$SO$_4$, filtered and concentrated to give 4-[[3-isopropyl-1-(p-tolylsulfonyl)pyrrolo[3,2-b]pyridin-5-yl]methyl]-3,5-dimethyl-aniline (120 mg, 0.261 mmol, 84.22% yield, 98% purity) as a light yellow solid. $^1$H NMR (400 MHz, CDCl$_3$) δ 7.90 (d, J=8.6 Hz, 1H), 7.62 (d, J=8.4 Hz, 2H), 7.36 (d, J=0.9 Hz, 1H), 7.14 (d, J=8.1 Hz, 2H), 6.64 (d, J=8.6 Hz, 1H), 6.37 (s, 2H), 4.10 (s, 2H), 3.45 (br s, 2H), 3.29-3.15 (m, 1H), 2.28 (s, 3H), 2.11 (s, 6H), 1.28 (d, J=6.9 Hz, 6H). LC-MS Method B, Rt: 1.139, (ESI, m/z): 448 [M+H]$^+$.

To a solution of 5-oxo-4H-1,2,4-oxadiazole-3-carboxylic acid (200 mg, 1.54 mmol) in THF (6 mL) was added (COCl)$_2$ (234.23 mg, 1.85 mmol, 0.162 mL) in DMF (1 mL) at 20° C. The mixture was stirred at 20° C. for 2 h. The reaction mixture was concentrated to give 5-oxo-4H-1,2,4-oxadiazole-3-carbonyl chloride (184 mg, crude) as a yellow oil, which was used in next step without further purification.

To a solution of 4-[[3-isopropyl-1-(p-tolylsulfonyl)pyrrolo[3,2-b]pyridin-5-yl]methyl]-3,5-dimethyl-aniline (150 mg, 0.335 mmol) and Et$_3$N (67.82 mg, 0.670 mmol, 0.093 mL) in THF (8 mL) was added 5-oxo-4H-1,2,4-oxadiazole-3-carbonyl chloride (74.65 mg, 0.503 mmol) at 20° C. The mixture was stirred at 20° C. for 12 h. The reaction mixture was concentrated to give N-[4-[[3-isopropyl-1-(p-tolylsulfonyl)pyrrolo[3,2-b]pyridin-5-yl]methyl]-3,5-dimethyl-phenyl]-5-oxo-4H-1,2,4-oxadiazole-3-carboxamide (456 mg, crude) as a yellow solid, which was used in next step without further purification. LC-MS Method A, Rt: 3.075, (ESI, m/z): 560[M+H]$^+$.

To a solution of N-[4-[[3-isopropyl-1-(p-tolylsulfonyl)pyrrolo[3,2-b]pyridin-5-yl]methyl]-3,5-dimethyl-phenyl]-5-oxo-4H-1,2,4-oxadiazole-3-carboxamide (456 mg, 0.611 mmol, 75% purity) in THF (10 mL) was added TBAF (1 M, 3.67 mL) at 20° C. After the addition, the mixture was stirred at 65° C. for 12 h. The reaction mixture was diluted with H₂O (20 mL), extracted with EA (2×20 mL). The combined organic layers were washed with brine (20 mL), dried over anhydrous Na₂SO₄, the solids were removed by filtration and the filtrate was concentrated under reduced pressure. The crude product was purified by preparatory HPLC (Column: Phenomenex luna C18, 80×40mm×3 um; Mobile phase: from 15% CH₃CN in water (0.05% HCl) to 45% CH₃CN in water (0.05% HCl)) to afford N-[4-[(3-isopropyl-1H-pyrrolo[3,2-b]pyridin-5-yl)methyl]-3,5-dimethyl-phenyl]-5-oxo-4H-1,2,4-oxadiazole-3-carboxamide (19.88 mg, 0.049 mmol, 8% yield, 99% purity) as a white solid. ¹H NMR (400 MHz, DMSO-d₆) δ 12.56-12.22 (m, 1H), 10.98-10.85 (m, 1H), 8.39-8.16 (m, 1H), 8.11-7.91 (m, 1H), 7.61-7.49 (m, 2H), 6.70-6.64 (m, 1H), 4.57-4.42 (m, 2H), 3.55-3.46 (m, 1H), 2.26-2.20 (m, 6H), 1.40-1.33 (m, 6H). LC-MS Method A, Rt: 1.546, (ESI, m/z): 406[M+H]⁺.

Example 4

Synthesis of Compound 4: 2-((4-((3-isopropyl-1H-pyrrolo[3,2-b]pyridin-5-yl)methyl)-3,5-dimethylphenyl)amino)-2-oxoacetic acid

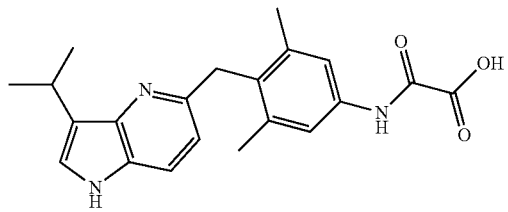 [SMILES: Cc1cc(NC(=O)C(=O)O)cc(C)c1Cc1ccc2[nH]cc(C(C)C)c2n1]

To a solution of 4-[[3-isopropyl-1-(mtolylsulfonyl)pyrrolo[3,2-b]pyridin-5-yl]methyl]-3,5-dimethyl-aniline (500 mg, 1.12 mmol) and Et₃N (430.62 mg, 4.26 mmol, 0.592 mL) in THF (20 mL) was added dropwise ethyl 2-chloro-2-oxo-acetate (145.26 mg, 1.06 mmol, 0.119 mL) at 20° C. After the addition, the mixture was stirred at 20° C. for 12 h. The reaction mixture was concentrated to give crude ethyl 2-[4-[[3-isopropyl-1-(p-tolylsulfonyl)pyrrolo[3,2-b]pyridin-5-yl]methyl]-3,5-dimethyl-anilino]-2-oxo-acetate (661 mg, crude) as a yellow solid, which was directly used in the next step without further purification. ¹H NMR (400 MHz, DMSO-d₆) δ 10.56 (s, 1H), 8.16-8.09 (m, 1H), 7.85 (d, J=8.4 Hz, 2H), 7.71 (s, 1H), 7.44-7.34 (m, 4H), 6.93 (d, J=8.6 Hz, 1H), 4.29 (q, J=7.1 Hz, 2H), 4.16 (s, 2H), 3.15-3.08 (m, 1H), 2.30 (s, 3H), 2.25 (s, 6H), 1.33-1.29 (m, 3H), 1.27 (d, J=7.0 Hz, 6H). LC-MS Method A, Rt: 1.193, (ESI, m/z): 548 [M+H]⁺.

To a solution of crude ethyl 2-[[3-isopropyl-1-(p-tolylsulfonyl)pyrrolo[3,2-b]pyridin-5-yl]methyl]-3,5-dimethyl-anilino]-2-oxo-acetate (661 mg, 1.21 mmol) in THF (20 mL) was added TBAF (1 M, 8.45 mL) at 20° C. After the addition, the mixture was stirred at 60° C. for 12 h. The reaction mixture was diluted with NH₄Cl (sat., aq., 30 mL), extracted with EA (2×30 mL). The combined organic layers were washed with brine (30 mL), dried over anhydrous Na₂SO₄, the solids were removed by filtration and the filtrate was concentrated under reduced pressure. The crude product was purified by preparatory HPLC (Column: Phenomenex luna C18, 80×40 mm×3 um; Mobile phase: from 20% CH3CN in water (0.05% HCl) to 50% CH₃CN in water (0.05% HCl)) to afford 2-[4-[(3-isopropyl-1H-pyrrolo[3,2-b]pyridin-5-yl)methyl]-3,5-dimethyl-anilino]-2-oxo-acetic acid (54.47 mg, 0.149 mmol, 12% yield) as a white solid. ¹H NMR (400 MHz, DMSO-d₆) δ 12.54-11.31 (m, 1H), 10.57 (s, 1H), 8.14-7.71 (m, 2H), 7.51 (s, 2H), 6.65 (d, J=8.4 Hz, 1H), 4.39 (br s, 2H), 3.40-3.39 (m, 1H), 2.24 (s, 6H), 1.35 (d, J=6.8 Hz, 6H) LC-MS Method A, Rt: 0.651, (ESI, m/z): 366[M+H]⁺.

Example 5

Synthesis of Compound 5: ethyl 2-((4-((3-isopropyl-1H-pyrrolo[3,2-b]pyridin-5-yl)methyl)-3,5-dimethylphenyl)amino)-2-oxoacetate

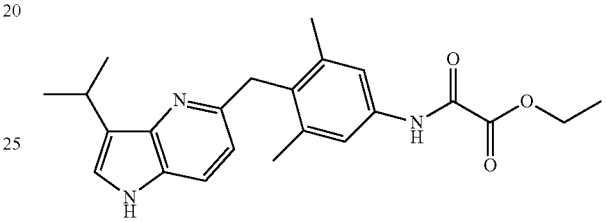

To a solution of 4-[[3-isopropyl-1-(p-tolylsulfonyl)pyrrolo[3,2-b]pyridin-5-yl]methyl]-3,5-dimethyl-aniline (300 mg, 0.670 mmol) in THF (20 mL) was added TBAF (1 M, 3.35 mL) at 20° C. After the addition, the mixture was stirred at 60° C. for 12 h. The reaction mixture was diluted with saturated aq. NH₄Cl (20 mL) and extracted with EA (2×20 mL). The combined organic layers were washed with brine (20 mL), dried over anhydrous Na₂SO₄, the solids were removed by filtration and the filtrate was concentrated under reduced pressure. The crude product was purified by silica gel chromatography (eluent: 0~50% EA/PE) to give 4-[(3-isopropyl-1H-pyrrolo[3,2-b]pyridin-5-yl)methyl]-3,5-dimethyl-aniline (74 mg, 0.238 mmol, 36% yield, 94% purity) as a yellow solid. LC-MS Method A, Rt: 0.487, (ESI, m/z): 294[M+H]⁺.

To a solution of 4-[(3-isopropyl-1H-pyrrolo[3,2-b]pyridin-5-yl)methyl]-3,5-dimethyl-aniline (74 mg, 0.252 mmol) in THF (5 mL) was added ethyl 2-chloro-2-oxo-acetate (34.44 mg, 0.252 mmol, 0.028 mL) and Et₃N (0.378 mmol, 0.053 mL) at 20° C. After the addition, the mixture was stirred at 20° C. for 12 h. The reaction mixture was diluted with H₂O (20 mL) and extracted with EA (2×20 mL). The combined organic layers were washed with brine (20 mL), dried over anhydrous Na₂SO₄, the solids were removed by filtration and the filtrate was concentrated under reduced pressure. The crude product was purified by preparatory HPLC (Column: Phenomenex luna C18 80×40 mm×3 um; Mobile phase: from 15% CH₃CN in water (0.05% HCl) to 45% CH₃CN in water (0.05% HCl)) to afford ethyl 2-[4-[(3-isopropyl-1H-pyrrolo[3,2-b]pyridin-5-yl)methyl]-3,5-dimethyl-anilino]-2-oxo-acetate (46.55 mg, 0.118 mmol, 47% yield) as a white solid. ¹H NMR (400 MHz, DMSO-d₆) δ 12.44 (br s, 1H), 10.70 (br s, 1H), 8.41-7.98 (m, 2H), 7.52 (s, 2H), 6.67 (d, J=8.5 Hz, 1H), 4.53 (br s, 2H), 4.32 (q, J=7.1 Hz, 2H), 2.21 (s, 6H), 1.39-1.29 (m, 9H). LC-MS Method A, Rt: 1.724, (ESI, m/z): 394[M+H]⁺.

Example 6

Synthesis of Compound 6: [[5-([3-isopropyl-1H-pyrrolo[3,2-b]pyridin-5-yl]methyl)-3,4,6-trimethylpyridin-2-yl]oxy]acetic acid

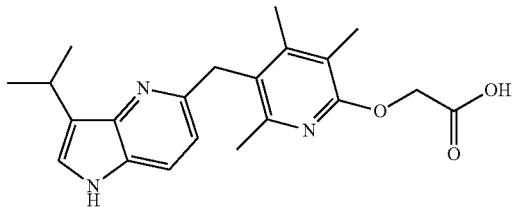 [SMILES: Cc1nc(OCC(=O)O)c(C)c(C)c1Cc1ccc2[nH]cc(C(C)C)c2n1]

A solution of sodium nitrite (3.99 g, 57.8 mmol) was added dropwise to a stirred solution of 6-bromopyridin-3-amine (10.0 g, 57.8 mmol) in HCl (6 M aq., 200 mL) at 0° C. The reaction mixture was stirred for 0.5 hour at 0° C. Then a solution of stannous chloride (32.6 g, 144.5 mmol) in HCl (6 M, 200 mL) was added to the reaction mixture at 0° C. and stirred for 0.5 hour. The reaction mixture is basified to pH 10 with NaOH (1M, aq.), the solid was removed by filtration, and the aqueous layer is extracted with EA (3×200 mL). The organic layers are combined, dried over sodium sulfate and concentrated under vacuo to afford the crude product, which was purified by silica gel chromatography PE/EA (1/99) to afford 2-bromo-5-hydrazinylpyridine (6 g, 55%) as a white solid. LC-MS (ESI, m/z): 188 [M+H]$^+$.

To a solution of 2-bromo-5-hydrazinylpyridine (6 g, 31.9 mmol) was suspended in 5% v/v sulfuric acid (5 mL) in water (100 mL) to form a suspension. Isovaleraldehyde (3.02 g, 35.1 mmol) was added and the suspension was stirred for 20 min at room temperature, then heated with a reflux condenser at 110° C. for overnight. Upon completion, the mixture was cooled in an ice bath. The reaction was quenched via the addition of 40%w/w aq. solution of KOH until the pH was basic. The reaction mixture was extracted with CH$_2$Cl$_2$ (3×100 mL). The combined organic layers were washed with brine (100 mL), dried over anhydrous sodium sulfate, filtered and concentrated under reduced pressure. The residue was chromatographed on a silica gel column with PE/EA (89/11) to provide 5.76 g (yield 75%) of 5-bromo-3-isopropyl-1H-pyrrolo[3,2-b]pyridine as a yellow solid. LC-MS (ESI, m/z): 239 [M+H]+.

A solution of 5-bromo-3-isopropyl-1H-pyrrolo[3,2-b]pyridine (1.80 g, 7.53 mmol), p-toluenesulfonyl chloride (2.87 g, 15.1 mmol), N,N-dimethylpyridin-4-amine (18.4 mg, 0.151 mmol) and N-ethyl-N-isopropylpropan-2-amine (2.14 g, 16.6 mmol) in CH$_2$Cl$_1$ (10 mL) was stirred for overnight at room temperature under nitrogen atmosphere. The resulting mixture was concentrated under reduced pressure. The residue was chromatographed on a silica gel column with PE/EA (10/1) to afford 5-bromo-3-isopropyl-1-(4-methylbenzenesulfonyl)pyrrolo[3,2-b]pyridine (1.5 g, 51%) as a white solid. LC-MS (ESI, m/z): 393 [M+H]+.

A 250 mL round-bottom flask was charged with 4,6-dimethylpyridin-2-ol (7 g, 56.8 mmol), t-butyl-peroxide (24.9 g, 170 mmol) and acetic acid (90 mL) at room temperature. The resulting mixture was stirred for overnight at 120° C. under nitrogen atmosphere and concentrated under reduced pressure. The residue was purified by silica gel column chromatography, eluted with CH$_2$Cl$_2$/CH$_3$OH (9/1) to afford 3,4,6-trimethylpyridin-2-ol (1.8 g, 23%) as a yellow solid. LC-MS (ESI, m/z): 138 [M+H]+.

A 250 mL round-bottom flask was charged with 3,4,6-trimethylpyridin-2-ol (1.8 g, 13.1 mmol), t-butyl 2-bromoacetate (7.68 g, 39.4 mmol), Cs$_2$CO$_3$ (10.7 g, 32.8 mmol) and DMF (90 mL) at room temperature. The resulting mixture was stirred for overnight at 120° C. The reaction was quenched with water (100 mL). The resulting mixture was extracted with EA (3×100 mL). The combined organic layers were washed with brine (100 mL), dried over anhydrous sodium sulfate. After filtration, the filtrate was concentrated under reduced pressure. The crude was purified by silica gel column chromatography, eluted with PE/EA (10/1) to afford t-butyl 2-[(3,4,6-trimethylpyridin-2-yl)oxy]acetate (500 mg, 15%) as a colorless oil. LC-MS (ESI, m/z): 252 [M+H]+.

A 40 mL vial was charged with t-butyl 2-[(3,4,6-trimethylpyridin-2-yl)oxy]acetate (0.5 g, 1.99 mmol), chloroform (10 mL). NBS (0.49 g, 2.76 mmol) was added at 0° C. The resulting mixture was stirred for 2 h at room temperature. The reaction was quenched with water (10 mL). The resulting mixture was extracted with CH$_2$Cl$_2$ (3×20 mL). The combined organic layers were washed with brine (20 mL), dried over anhydrous sodium sulfate. After filtration, the filtrate was concentrated under reduced pressure. The residue was purified by silica gel column chromatography, eluted with PE/EA (10/1) to afford t-butyl 2-[(5-bromo-3,4,6-trimethylpyridin-2-yl)oxy]acetate (400 mg, 61%) as a colorless oil. $^1$HNMR (400 MHz, DMSO-d$_6$) δ 4.72 (s, 2H), 2.49 (s, 3H), 2.35 (m, 3H), 2.23 (s, 3H), 1.46 (s, 9H). LC-MS (ESI, m/z): 330 [M+H]+.

A 40 mL vial was charged with t-butyl 2-[(5-bromo-3,4,6-trimethylpyridin-2-yl)oxy]acetate (400 mg, 1.21 mmol), 4,4,5,5-tetramethyl-2-[(4,4,5,5-tetramethyl-1,3,2-dioxaborolan-2-yl)methyl]-1,3,2-dioxaborolane (649 mg, 2.42 mmol), Pd[(t-Bu)$_3$P]$_2$ (61.9 mg, 0.121 mmol), dioxane (16 mL), KOH (135 mg, 2.42 mmol), water (1 mL). The resulting mixture was stirred for overnight at 80° C. under nitrogen atmosphere and quenched with water (20 mL). The resulting mixture was extracted with EA (3×20 mL). The combined organic layers were washed with brine (20 mL), dried over anhydrous sodium sulfate. After filtration, the filtrate was concentrated under reduced pressure. The residue was purified by silica gel column chromatography, eluted with PE/EA (12/1) to afford t-butyl 2-([3,4,6-trimethyl-5-[(4,4,5,5-tetramethyl-1,3,2-dioxaborolan-2-yl)methyl]pyridin-2-yl]oxy)acetate (300 mg, 63%) as a colorless oil. LC-MS (ESI, m/z): 392 [M+H]+.

A solution of t-butyl 2-([3,4,6-trimethyl-5-[(4,4,5,5-tetramethyl-1,3,2-dioxaborolan-2-yl)methyl]pyridin-2-yl]oxy)acetate (200 mg, 0.511 mmol), 5-bromo-3-isopropyl-1-(4-methylbenzenesulfonyl)pyrrolo[3,2-b]pyridine (201 mg, 0.511 mmol), potassium phosphate (325 mg, 1.53 mmol), dichlorobis(tri-o-tolylphosphine)palladium(II) (60.3 mg, 0.077 mmol) in dioxane (10 mL) and water (1 mL) was stirred for overnight at 110° C. under nitrogen atmosphere and quenched with (20 mL). The resulting mixture was extracted with EA (3×20 mL). The combined organic layers were washed with brine (20 mL), dried over anhydrous sodium sulfate. After filtration, the filtrate was concentrated under reduced pressure. The residue was purified by silica gel column chromatography, eluted with PE/EA (16/1) to afford tert-butyl 2-[(5-[[3-isopropyl-1-(4-methylbenzenesulfonyl)pyrrolo[3,2-b]pyridin-5-yl]methyl]-3,4,6-trimethylpyridin-2-yl)oxy]acetate (140 mg, 47%) as a yellow oil. LC-MS (ESI, m/z): 578 [M+H]+.

A solution of t-butyl 2-[(5-[[3-isopropyl-1-(4-methylbenzenesulfonyl)pyrrolo[3,2-b]pyridin-5-yl]methyl]-3,4,6-trimethylpyridin-2-yl)oxy]acetate (140 mg, 0.242 mmol) and tetrabutylammonium fluoride (317 mg, 1.21 mmol) in THF (3 mL) was stirred overnight at 65° C. and then quenched with water (20 mL). The resulting mixture was extracted with EA (3×30 mL). The combined organic layers were washed with brine (30 mL), dried over anhydrous sodium sulfate. After filtration, the filtrate was concentrated under reduced pressure. The residue was purified by silica gel column chromatography, eluted with PE/EA (9/1) to afford t-butyl 2-[[5-([3-isopropyl-1H-pyrrolo[3,2-b]pyridin-5-yl]methyl)-3,4,6-trimethylpyridin-2-yl]oxy]acetate (40 mg, 39%) as a colorless oil. LC-MS (ESI, m/z): 424 [M+H]+.

A solution of t-butyl 2-[[5-([3-isopropyl-1H-pyrrolo[3,2-b]pyridin-5-yl]methyl)-3,4,6-trimethylpyridin-2-yl]oxy]acetate (40 mg, 0.094 mmol) and HCl (conc., 0.2 mL) in dioxane (3 mL) was stirred for 3 h at room temperature and concentrated under reduced pressure. The crude was purified by prep-HPLC with the following conditions: Xbridge Phenyl OBD Column, 5 μm, 19×150 mm; Mobile Phase A: water (50 mmol/L $NH_4HCO_3$), Mobile Phase B: $CH_3CN$; Flow rate: 60 mL/min. This purification provided 22.2 mg [[5-([3-isopropyl-1H-pyrrolo[3,2-b]pyridin-5-yl]methyl)-3,4,6-trimethylpyridin-2-yl]oxy]acetic acid as a white solid. $^1$H NMR (400 MHz, DMSO-$d_6$) δ 10.80 (s, 1H), 7.54 (d, J=8.0 Hz, 1H), 7.28 (d, J=2.0 Hz, 1H), 6.65 (d, J=8.0 Hz, 1H), 4.72 (s, 2H), 4.14 (s, 2H), 3.17-3.22 (m, 1H), 2.33-2.34 (s, 3H), 2.32-2.33 (s, 3H), 2.10-2.32 (s, 3H), 1.32 (d, J=8.0 Hz, 6H). LC-MS Method E, Rt: 0.698, (ESI, m/z): 368[M+H]$^+$.

Preparation of 4-[[3-isopropyl-1-(4-methylbenzenesulfonyl)pyrrolo[3,2-b]pyridin-5-yl]methyl]-2,3,5-trimethylphenol.

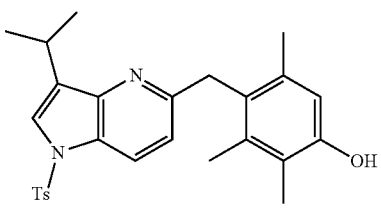 [SMILES: Cc1ccc(S(=O)(=O)n2cc(C(C)C)c3nc(Cc4c(C)cc(O)c(C)c4C)ccc32)cc1]

Into a 1L round-bottom flask, was placed 2-bromo-5-fluoropyridine (120 g, 682 mmol) in $NH_2NH_2$·$H_2O$ (300 mL). The resulting solution was stirred for 3 h at 110° C. The product was precipitated by the addition of water. The solids were collected by filtration. This resulted in 70 g (55%) of 2-bromo-5-hydrazinylpyridine as a white solid.

Into a 1L round-bottom flask was placed 2-bromo-5-hydrazinylpyridine (70 g, 372 mmol), ethanol (0.5 L), isovaleraldehyde (38.5 g, 447 mmol). The resulting solution was stirred for 1 h at 0° C., then concentrated to afford 55 g (58%) of 2-bromo-5-[2-(3-methylbutylidene)hydrazin-1-yl]pyridine as a yellow solid.

Into a 1L round-bottom flask was placed 2,3,5-trimethylphenol (55.0 g, 404 mmol), $CH_3CN$ (400 mL), and NBS (57.5 g, 323 mmol). The resulting solution was stirred for 5 h at 0° C., then concentrated under reduced pressure, and treated with water (200 mL). The solids were collected by filtration, washed with 800 mL of water, and air dried to afford 75 g (86%) of 4-bromo-2,3,5-trimethylphenol as a white solid.

Into a 1L round-bottom flask, was placed 2-bromo-5-[2-(3-methylbutylidene)hydrazin-1-yl]pyridine (55.0 g, 215 mmol), xylene (450 mL), $ZnCl_2$ (58.5 g, 429 mmol). The resulting solution was stirred overnight at 130° C. The resulting solution was cooled to rt, extracted with EA (3×500 mL). The combined organic layers were washed with brine (3×500 mL) and concentrated under reduced pressure. The crude was purified via a silica gel column (EA/PE=1/2) to afford 34 g (66%) of 5-bromo-3-isopropyl-1H-pyrrolo[3,2-b]pyridine as a yellow solid.

Into a 1L round-bottom flask was placed 4-bromo-2,3,5-trimethylphenol (75.0 g, 349 mmol), $CH_3CN$ (600 mL), $K_2CO_3$ (144.6 g, 1046 mmol), benzyl bromide (28.3 mL). The resulting solution was stirred for 20 h at room temperature, then diluted with EA (1L), and washed with water (3×500 mL). The organic layer was dried over anhydrous $MgSO_4$. The solids were removed by filtration and the filtrate was concentrated under reduced pressure. The crude product was purified via silica gel column chromatography (PE) to afford 70 g of 1-(benzyloxy)-4-bromo-2,3,5-trimethylbenzene as a white solid.

Into a 1L, 3-necked, round-bottom flask purged and maintained with an inert atmosphere of nitrogen, was placed 5-bromo-3-isopropyl-1H-pyrrolo[3,2-b]pyridine (34.0 g, 142 mmol), $CH_2Cl_2$ (520 mL), TsCl (54.2 g, 284 mmol), DMAP (347 mg, 2.84 mmol), DIEA (40.4 g, 313 mmol). The resulting solution was stirred overnight at room temperature, then was concentrated under reduced pressure. The crude product was purified via silica gel column chromatography (EA/PE=1/10) to afford 20 g of 5-bromo-3-isopropyl-1-(4-methylbenzenesulfonyl)pyrrolo[3,2-b]pyridine as a yellow solid.

Into a 1L, 3-necked, round-bottom flask, purged and maintained with an inert atmosphere of nitrogen, was placed 1-(benzyloxy)-4-bromo-2,3,5-trimethylbenzene (70.0 g, 229 mmol), bis(4,4,5,5-tetramethyl-1,3,2-dioxaborolan-2-yl) methane (67.60 g, 252 mmol), Pd(t-$Bu_3$P)$_2$ (11.7 g, 22.9 mmol), KOH (23.2 g, 413 mmol), 1,4-dioxane (500 mL), water (20 mL). The resulting solution was stirred overnight at 80° C. The reaction mixture was cooled to room temperature, treated with water (200 mL), extracted with EA (3×200 mL). The combined organic layers were washed with brine (3×500 mL), dried over anhydrous $MgSO_4$, the solids were removed by filtration and the filtrate was concentrated under reduced pressure. The crude product was purified via silica gel column chromatography (EA/PE=1/10) to afford 38 g of 2-[[4-(benzyloxy)-2,3,6-trimethylphenyl]methyl]-4,4,5,5-tetramethyl-1,3,2-dioxaborolane as yellow oil.

Into a 1L, 3-necked, round-bottom flask, purged and maintained with an inert atmosphere of nitrogen, was placed 5-bromo-3-isopropyl-1-(4-methylbenzenesulfonyl)pyrrolo[3,2-b]pyridine (20.0 g, 50.9 mmol), 2-[[4-(benzyloxy)-2,3,6-trimethylphenyl]methyl]-4,4,5,5-tetramethyl-1,3,2-dioxaborolane (37.3 g, 102 mmol), PdCl$_2$[P(o-Tol)]$_3$ (5.6 g, 7.1 mmol), potassium phosphate tribasic (32.4 g, 153 mmol), 1,4-dioxane (0.5 L), water (60 mL). The resulting solution was stirred overnight at 100° C. The solids were removed by filtration and the filtrate was concentrated under reduced pressure. The crude product was purified via silica gel column chromatography (EA/PE=1/10) to afford 5-[[4-(benzyloxy)-2,3,6-trimethylphenyl]methyl]-3-isopropyl-1-(4-methylbenzenesulfonyl)pyrrolo[3,2-b]pyridine (15 g) as yellow oil.

Into a 1L, 3-necked, round-bottom flask purged and maintained with an inert atmosphere of nitrogen, was placed 5-[[4-(benzyloxy)-2,3,6-trimethylphenyl]methyl]-3-isopropyl-1-(4-methylbenzenesulfonyl)pyrrolo [3,2-b]pyridine (13.0 g, 23.5 mmol) in $CH_2Cl_2$ (400 mL) was added $BBr_3$ (118 mL, 118 mmol, 1 M) at 0° C. The resulting solution was stirred overnight at room temperature, then quenched with $NaHCO_3$ (aq.) and extracted with $CH_2Cl_2$ (4×150 mL), the combined organic layers were concentrated in vacuo. The residue was purified by reverse phase chromatography C18 ($CH_3CN$/water (0.05% $NHHCO_3$)=10-90% in 30 min) to afford 4-[[3-isopropyl-1-(4-methylbenzenesulfonyl)pyrrolo[3,2-b]pyridin-5-yl]methyl]-2,3,5-trimethylphenol (10.03 g, 92%) as a yellow solid. LC-MS (ESI, m/z): 463[M+H]$^{30}$ $^1$H NMR (400 MHz, $CDCl_3$) δ 7.98 (d, J=4 Hz, 1H), 7.71 (d, J=8.4 Hz, 2H), 7.52 (d, J=27.6 Hz, 1H), 7.26-7.21 (m, 2H), 6.69 (d, J=8.4 Hz, 1H), 6.55 (s, 1H), 4.62 (s, 1H), 4.24 (s, 2H), 3.29 (s, 1H), 2.35-2.30 (m, 3H), 2.21 (s, 3H), 2.16 (d, J=7.2 Hz, 6H), 1.39-1.35 (m, 6H).

Example 7

Synthesis of Compound 7: 2-(4-((3-isopropyl-1H-pyrrolo[3,2-b]pyridin-5-yl)methyl)-2,3,5-trimethylphenoxy)propanoic acid Ethyl 2-bromopropionate (352.2 mg, 0.25 mL, 1.95 mmol) was added to a mixture of 4-((3 sopropyl-1H-pyrrolo[3,2-b]pyridin-5-yl)methyl)-2,3,5-trimethylphenol (500 mg, 1.081 mmol) and $Cs_2CO_3$ (528.2 mg, 1.62 mmol) in anhydrous $CH_3CN$ (10 mL) under Na. The reaction mixture was stirred at room temperature for 3 h. The reaction mixture was then diluted with EA, washed with brine and dried over $Na_2SO_4$. The solids were removed by filtration and the filtrate was evaporated to dryness. The crude product was purified by flash chromatography on silica gel (0% to 30% EA in CyH) to afford ethyl 2-(4-((3-isopropyl-1-tosyl-1H-pyrrolo[3,2-b]pyridin-5-yl)methyl)-2,3,5-trimethylphenoxy)propanoate (572 mg, 94%) as a white solid. $^1$H-NMR (DMSO-$d_6$, 300 MHz): 1.16 (t, J=6.9 Hz, 3H), 1.28 (d, J=6.9 Hz, 6H), 1.49 (d, J=6.6 Hz, 3H), 2.08 (s, 3H), 2.11 (s, 3H), 2.22 (s, 3H), 2.29 (s, 3H), 3.06-3.16 (m, 1H), 4.09-4.16 (m, 4H), 4.82 (q, J=6.9 Hz, 1H), 6.53 (s, 1H), 6.84 (d, J=8.4 Hz, 1H), 7.35 (d, J=7.8 Hz, 2H), 7.70 (s, 1H), 7.85 (d, J=7.8 Hz, 2H), 8.09 (d, J=8.4 Hz, 1H) ppm. LC-MS: $C_{32}H_{38}N_2O_5S$ [M+H]$^+$: 563.

A solution of KOH (1726 mg, 30.76 mmol) in $H_2O$ (25 mL) was added to a solution of ethyl 2444(3 sopropyl-1-tosyl-1H-pyrrolo[3,2-b]pyridin-5-yl)methyl)-2,3,5-trimethylphenoxy) propanoate (577 mg, 1.025 mmol) in $CH_3OH$ (25 mL) under $N_2$. The reaction mixture was stirred at 80° C. for 3 h. The reaction mixture was then concentrated under reduced pressure to remove $CH_3OH$. The resulting aqueous solution was carefully acidified using HCl 37% to pH~6. The resulting precipitate was removed by filtration and the filtrate was extracted twice with EA/2-propanol (85:15). The combined organic layers were evaporated to dryness and the resulting solid was triturated in EtOH to give 2-(4-((3-isopropyl-1H-pyrrolo[3,2-b]pyridin-5-yl)methyl)-2,3,5-trimethylphenoxy)propanoic acid (267 mg, 68%) as a white solid. $^1$H-NMR (DMSO-$d_6$, 400 MHz): 1.31 (d, J=6.9 Hz, 6H), 1.48 (d, J=6.7 Hz, 3H), 2.08 (s, 3H), 2.14 (s, 3H), 2.24 (s, 3H), 3.15-3.24 (m, 1H), 4.12 (s, 2H), 4.70 (q, J=6.8 Hz, 1H), 6.48-6.55 (m, 2H), 7.22-7.27 (m, 1H), 7.49 (d, J=8.4 Hz, 1H), 10.75 (br s, 1H) ppm. LC-MS Method D, Rt: 7.967, (ESI, m/z): 381 [M+H]$^+$.

Example 8

Synthesis of Compound 8: 2-(4-((3-isopropyl-1H-pyrrolo[3,2-b]pyridin-5-yl)methyl)-2,3,5-trimethylphenoxy)-2-methylpropanoic acid Ethyl 2-bromoisobutyrate (379.5 mg, 1.95 mmol) was added to a mixture of 2,3,5-trimethyl-4-{[1-(4-methylbenzenesulfonyl)-3-(propan-2-yl)-1H-pyrrolo[3,2-b]pyridin-5-yl]methyl}phenol (500 mg, 1.081 mmol) and $Cs_2CO_3$ (704.3 mg, 2.16 mmol) in anhydrous $CH_3CN$ (10 mL) under $N_2$. The reaction mixture was stirred at room temperature for 1 h and at 40° C. for 3 h. After cooling to room temperature, the reaction mixture was diluted with EA. The solids were removed by filtration and the filtrate was evaporated to dryness. The crude product was purified by flash chromatography on silica gel (15% EA in CyH) to give ethyl 2-(4-((3-isopropyl-1-tosyl-1H-pyrrolo[3,2-b]pyridin-5-yl)methyl)-2,3,5-trimethylphenoxy)-2-methylpropanoate (478 mg, 77%) as a colorless oil. $^1$H-NMR (DMSO-$d_6$, 300 MHz): 1.19 (t, J=6.9 Hz, 3H), 1.29 (d, J=6.9 Hz, 6H), 1.49 (s, 6H), 2.08 (s, 3H), 2.13 (s, 3H), 2.21 (s, 3H), 2.32 (s, 3H), 3.06-3.16 (m, 1H), 4.16 (s, 2H), 4.19 (q, J=6.9 Hz, 2H), 4.82 (q, J=6.9 Hz, 1H), 6.41 (s, 1H), 6.89 (d, J=8.7 Hz, 1H), 7.38 (d, J=7.8 Hz, 2H), 7.72 (s, 1H), 7.87 (d, J=7.8 Hz, 2H), 8.11 (d, J=8.4 Hz, 1H) ppm. LC-MS: $C_{33}H_{40}N_2O_5S$ [M+H]$^+$: 577.

A solution of KOH (1021 mg, 18.205 mmol) in water (15 mL) was added to a solution of 2-(4-((3-isopropyl-1-tosyl-1H-pyrrolo[3,2-b]pyridin-5-yl) methyl)-2,3,5-trimethylphenoxy)-2-methylpropanoate (350 mg, 0.607 mmol) in methanol (15 mL) under $N_2$. The reaction mixture was heated at 80° C. for 3 days. After cooling to room temperature, the reaction mixture was diluted with water (20 mL) and acidified to pH 6 using HCl (1M, aq.). The resulting precipitate was collected by filtration and dried under high vacuum to give 2-(4-((3-isopropyl-1H-pyrrolo[3,2-b]pyridin-5-yl)methyl)-2,3,5-trimethylphenoxy)-2-methylpropanoic acid (100 mg, 42%) as a white solid. $^1$H-NMR (DMSO-$d_6$, 400 MHz): 1.32 (d, J=6.7 Hz, 6H), 1.47 (s, 6H), 2.07 (s, 3H), 2.15 (s, 3H), 2.23 (s, 3H), 3.16-3.25 (m, 1H), 4.14 (s, 2H), 6.52 (s, 1H), 6.56 (d, J=8.4 Hz, 1H), 7.26 (s, 1H), 7.52 (d, J=8.2 Hz, 1H), 10.77 (s, 1H) ppm. LC-MS: $C_{24}H_{30}N_2O_3$ [M+H]$^+$: 395. LC-MS Method D, Rt: 8.091, (ESI, m/z): 395[M+H]$^+$.

Example 9

Synthesis of Compound 9: 2-fluoro-2-(4-((3-isopropyl-1H-pyrrolo[3,2-b]pyridin-5-yl)methyl)-2,3,5-trimethylphenoxy)acetic acid

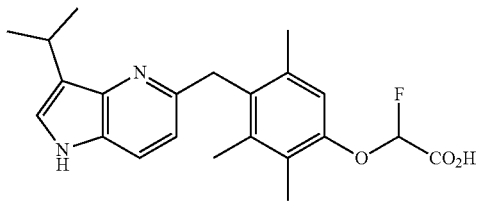 [SMILES: Cc1cc(OC(F)C(=O)O)c(C)c(C)c1Cc1ccc2[nH]cc(C(C)C)c2n1]

Ethyl bromofluoroacetate (300 mg, 1.62 mmol) was added to a mixture of 2,3,5-trimethyl-4-{[1-(4-methylbenzenesulfonyl)-3-(propan-2-yl)-1H-pyrrolo[3,2-b]pyridin-5-yl]methyl}phenol (500 mg, 1.081 mmol) and $Cs_2CO_3$ (704.3 mg, 2.16 mmol) in anhydrous $CH_3CN$ (10 mL) under $N_2$. The reaction mixture was stirred at room temperature for 2 h. The reaction mixture was then diluted with EA. The solids were removed by filtration and the filtrate was evaporated to dryness. The crude product was purified by flash chromatography on silica gel (20% EA in CyH) to afford ethyl 2-fluoro-2-(4-((3-isopropyl-1-tosyl-1H-pyrrolo[3,2-b]pyridin-5-yl)methyl)-2,3,5-trimethylphenoxy)acetate (499 mg, 81%) as a colorless oil. $^1$H-NMR (DMSO-$d_6$, 300 MHz): 1.24-1.29 (m, 6H), 1.49 (d, J=6.6 Hz, 3H), 2.10 (s, 3H), 2.16 (s, 3H), 2.29 (s, 3H), 2.31 (s, 3H), 3.06-3.16 (m, 1H), 4.19 (s, 2H), 4.23-4.34 (m, 2H), 6.27 (d, J=59 Hz, 1H), 6.87-6.91 (m, 2H), 7.37 (d, J=7.8 Hz, 2H), 7.71 (s, 1H), 7.86 (d, J=7.8 Hz, 2H), 8.11 (d, J=8.4 Hz, 1H) ppm. LC-MS: $C_{31}H_{35}FN_2O_5S$ [M+H]$^+$: 567.

A solution of KOH (1185 mg, 21.12 mmol) in water (16 mL) was added to a solution of 2-fluoro-2-(4-((3-isopropyl-1-tosyl-1H-pyrrolo [3,2-b]pyridin-5-yl)methyl)-trimethylphenoxy)acetate (399 mg, 0.704 mmol) in $CH_3OH$ (16 mL) under $N_2$. The reaction mixture was stirred at 80° C. for 2 h. After cooling to room temperature, the reaction was concentrated under reduced pressure. The resulting solution was acidified to pH=6 with conc. HCl and the precipitate was collected by filtration. The crude product was purified by prep. HPLC (20% to 100% $CH_3CN$ in water [0.2% v/v $NH_4OAc$]) to give 2-fluoro-2-(4-((3-isopropyl-1H-pyrrolo[3,2-b]pyridin-5-yl)methyl)-2,3,5-trimethylphenoxy)acetic acid (29.7 mg, 11%) as a white solid. $^1$H-NMR (DMSO-$d_6$, 400 MHz): 1.33 (d, J=6.9 Hz, 6H), 2.12 (s, 3H), 2.20 (s, 3H), 2.32 (s, 3H), 3.18-3.25 (m, 1H), 4.19 (s, 2H), 6.11 (d, J=60 Hz, 1H), 6.57 (d, J=8.4 Hz, 1H), 6.90 (s, 1H), 7.29 (d, J=2.1 Hz, 1H), 7.53 (d, J=8.4 Hz, 1H), 10.81 (s, 1H) ppm. LC-MS Method D, Rt: 7.476, (ESI, m/z): 385[M+H]$^+$.

Example 10

Synthesis of Compound 10: 5-(4-((2H-tetrazol-5-yl)methoxy)-2,3,6-trimethylbenzyl)-3-isopropyl-1H-pyrrolo[3,2-b]pyridine

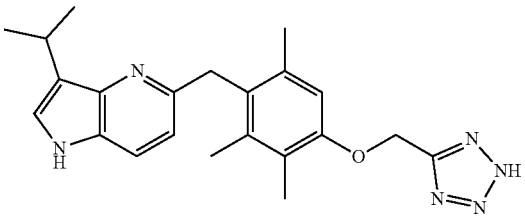 [SMILES: Cc1cc(OCc2nn[nH]n2)c(C)c(C)c1Cc1ccc2[nH]cc(C(C)C)c2n1]

Bromoacetonitrile (194 mg, 1.62 mmol) was added dropwise to a mixture of 2,3,5-trimethyl-4-{[1-(4-methylbenzenesulfonyl)-3-(propan-2-yl)-1H-pyrrolo[3,2-b]pyridin-5-yl]methyl}phenol (500 mg, 1.081 mmol) and $K_2CO_3$ (224 mg, 1.62 mmol) in DMF (5 mL) under $N_2$. The reaction mixture was stirred at room temperature for 20 h. The reaction mixture was then diluted with EA and water. The layers were separated and the organic layer was washed with water and brine and dried over $MgSO_4$. The solids were removed by filtration and the filtrate was evaporated to dryness. The crude product was purified by flash chromatography on silica gel (0% to 5% $CH_3OH$ in $CH_2Cl_2$) to give 2-(4-((3-isopropyl-1-tosyl-1H-pyrrolo[3,2-b]pyridin-5-yl)methyl)-2,3,5-trimethylphenoxy)acetonitrile (301 mg, 56%) as a dark oil. $^1$H-NMR (DMSO-$d_6$, 300 MHz): 1.29 (d, J=6.6 Hz, 6H), 2.07 (s, 3H), 2.14 (s, 3H), 2.30 (s, 3H), 2.31 (s, 3H), 3.06-3.16 (m, 1H), 4.14 (s, 2H), 5.11 (s, 2H), 6.83 (s, 1H), 6.86 (d, J=8.7 Hz, 1H), 7.37 (d, J=7.8 Hz, 2H), 7.71 (s, 1H), 7.86 (d, J=7.8 Hz, 2H), 8.11 (d, J=8.7 Hz, 1H) ppm. LC-MS: $C_{29}H_{31}N_3O_3S$ [M+H]$^+$: 502.

AcOH (0.050 mL, 0.88 mmol) was added to a mixture of 2-(4-((3-isopropyl-1-tosyl-1H-pyrrolo[3,2-b]pyridin-5-yl)methyl)-2,3,5-trimethylphenoxy)acetonitrile (251 mg, 0.5003 mmol), $NaN_3$ (97.6 mg, 1.501 mmol) and $NH_4Cl$ (133.8 mg, 2.502 mmol) in DMF under $N_2$. The reaction mixture was stirred at 110° C. for 24 h. After cooling to room temperature, the reaction mixture was diluted with EA and sat. aq. $NaHCO_3$. The layers were separated and the aqueous layer was re-extracted with EA. The combined organic layers were washed with brine and dried over $Na_2SO_4$. The solids were removed by filtration and the filtrate was evaporated to dryness. The crude product was purified by flash chromatography on silica gel (10% to 20% [$CH_3OH$/$NH_4OH$ (9:1)] in $CH_2Cl_2$) to give 5-(4-((2H-tetrazol -5-yl)methoxy)-2,3,6-trimethylbenzyl)-3-isopropyl-1-tosyl-1H-pyrrolo[3,2-b]pyridine (168 mg, 62%) as a white solid.

A solution of KOH (92.7 mg, 1.65 mmol) in water (9 mL) was added to a solution of 5-(4-((2H-tetrazol -5-yl)methoxy)-2,3,6-trimethylbenzyl)-3 sopropyl-1-tosyl-1H-pyrrolo[3,2-b]pyridine (180 mg, 0.33 mmol) in $CH_3OH$ (9 mL). The reaction mixture was stirred at 80° C. for 16 h. After cooling to room temperature, the reaction mixture was diluted with EA and sat. aq. $NaHCO_3$. The layers were separated and the aqueous layer was re-extracted with EA (2×). The combined organic layers were evaporated to dryness. The residue was taken up in $CH_3OH$. The solids were removed by filtration and the filtrate was evaporated to dryness. The residue was taken up in EA, washed with water and brine and dried over $Na_2SO_4$. The solids were removed by filtration and the filtrate was evaporated to dryness. The resulting solid was triturated in Et$_2$O and dried under high vacuum to give 5-(4-((2H-tetrazol-5-yl)methoxy)-2,3,6-trimethylbenzyl)-3-isopropyl-1H-pyrrolo[3,2-b]pyridine (51 mg, 40%) as a white solid. $^1$H-NMR (DMSO-d$_6$, 600 MHz): 1.34 (d, J=6.9 Hz, 6H), 2.06 (s, 3H), 2.16 (s, 3H), 2.31 (s, 3H), 3.06-3.16 (m, 1H), 4.16 (s, 2H), 5.28 (s, 2H), 6.54 (d, J=8.6 Hz, 1H), 6.90 (s, 1H), 7.29 (d, J=2.3 Hz, 1H), 7.52 (d, J=8.4 Hz, 1H), 10.79 (s, 1H) ppm. LC-MS Method D, Rt: 7.506, (ESI, m/z): 391[M+H]$^+$.

Example 11

Synthesis of Compound 11: 3-((4-((3-isopropyl-1H-pyrrolo[3,2-b]pyridin-5-yl)methyl)-2,3,5-trimethylphenoxy)methyl)-1,2,4-oxadiazol-5(4H)-one

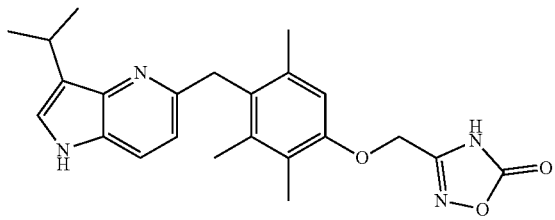 [SMILES: Cc1cc(OCc2noc(=O)[nH]2)c(C)c(C)c1Cc1ccc2[nH]cc(C(C)C)c2n1]

A mixture of 2-(4-((3 sopropyl-1-tosyl-1H-pyrrolo[3,2-b]pyridin-5-yl)methyl)-2,3,5-trimethylphenoxy)acetonitrile (260 mg, 0.52 mmol), hydroxylamine hydrochloride (54 mg, 0.78 mmol) and NaHCO$_3$ (152 mg, 1.81 mmol) in CH$_3$OH (5 mL) was stirred at 75° C. for 3 h under N$_2$. After cooling to room temperature, the reaction mixture was diluted with EA, washed with brine twice and dried over Na$_2$SO$_4$. The solids were removed by filtration and the filtrate was evaporated to dryness to give N'-hydroxy-2-(4-((3-isopropyl-1-tosyl-1H-pyrrolo[3,2-b]pyridin-5-yl)methyl)-2,3,5-trimethylphenoxy)acetimidamide (255 mg, 92%) as a colorless oil which was used as such in the next step. $^1$-NMR (DMSO-d$_6$, 300 MHz): 1.29 (d, J=6.7 Hz, 6H), 2.07 (s, 3H), 2.12 (s, 3H), 2.25 (s, 3H), 2.30 (s, 3H), 3.08-3.17 (m, 1H), 4.15 (s, 2H), 4.35 (s, 2H), 5.54 (s, 2H), 6.75 (s, 1H), 6.82 (d, J=8.4 Hz, 1H), 7.36 (d, J=8.4 Hz, 2H), 7.70 (s, 1H), 7.85 (d, J=8.4 Hz, 2H), 8.10 (d, J=8.4 Hz, 1H), 9.25 (s, 1H) ppm.

A mixture of N'-hydroxy-2-(4-((3-isopropyl-1-tosyl-1H-pyrrolo[3,2-b]pyridin-5-yl)methyl)-2,3,5-trimethylphenoxy)acetimidamide (255 mg, 0.48 mmol) and CDI (92.8 mg, 0.57 mmol) in anhydrous 1,4-dioxane (5 mL) was stirred at 100° C. for 19 h under N$_2$. After cooling to room temperature, the reaction mixture was diluted with EA, washed with brine (3×) and dried over Na$_2$SO$_4$. The solids were removed by filtration and the filtrate was evaporated to dryness to afford 3-((4-((3 sopropyl-1-tosyl-1H-pyrrolo[3,2-b]pyridin-5-yl)methyl)-2,3,5-trimethylphenoxy)methyl)-1,2,4-oxadiazol-5(4H)-one (267 mg, 100%) as a yellow oil which was used as such in the next step. LC-MS: C$_{30}$H$_{32}$N$_4$O$_5$S [M+H]$^+$: 561.

A solution of TBAF (1M in THF) (4.8 mL, 4.77 mmol) and 3-((4-((3-isopropyl-1-tosyl-1H-pyrrolo[3,2-b]pyridin-5-yl)methyl)-2,3,5-trimethylphenoxy)methyl)-1,2,4-oxadiazol-5(4H)-one (267 mg, 0.48 mmol) in anhydrous THF (6 mL) was stirred at 66° C. for 26 h under N$_2$. After cooling to room temperature, the reaction mixture was diluted with EA, washed with brine (3×) and dried over Na$_2$SO$_4$. The solids were removed by filtration and the filtrate was evaporated to dryness. The crude mixture was purified by flash chromatography on silica gel (0% to 10% methanol in CH$_2$Cl$_2$) to afford 3-((4-((3-isopropyl-1H-pyrrolo[3,2-b]pyridin-5-yl)methyl)-2,3,5-trimethylphenoxy)methyl)-1,2,4-oxadiazol-5(4H)-one (66 mg, 34%) as a yellow solid. $^1$H-NMR (DMSO-d$_6$, 300 MHz): 1.33 (d, J=6.7 Hz, 6H), 2.10 (s, 3H), 2.18 (s, 3H), 2.32 (s, 3H), 3.16-3.25 (m, 1H), 4.17 (s, 2H), 4.97 (s, 2H), 6.54 (d, J=8.3 Hz, 1H), 6.82 (s, 1H), 7.28 (d, J=2.3 Hz, 1H), 7.51 (d, J=8.3 Hz, 1H), 10.78 (s, 1H) ppm. LC-MS Method D, Rt: 7.768, (ESI, m/z): 407[M+H]$^+$ LC-MS Methods The following LC-MS conditions were used to assess the purity, retention time and [M+H]$^+$ or [M-H]$^-$ of the compounds disclosed herein (Table 1).

TABLE 1

| Method | Instrument | Column | Mobile phase | Gradient | Flow (mL/min) | Col. T (° C.) | Run time |
|---|---|---|---|---|---|---|---|
| A | Shimadzu LCMS2020 | Xtimate C18 2.1 × 30 mm, 3 μm | A: H$_2$O(4 L) + TFA(1.5 mL) B: CH$_3$CN (4 L) + TFA(0.75 mL) | From 90% A to 20% A in 0.9 minutes and holding at 20% for 0.6 minutes, to 90% A in 0.01 min held for 0.49 min | 1.2 | 50 | 2 |
| B | Shimadzu LCMS2020 | Xtimate C18 2.1 × 30 mm, 3 μm | A: H$_2$O (4 L) + TFA(1.5 mL) B: CH$_3$CN (4 L) + TFA(0.75 mL) | From 95% A to 5% A in 0.7 minutes and holding at 5% for 0.4 minutes, to 95% A in 0.01 min held for 0.49 min | 1.5 | 50 | 1.6 |
| C | Shimadzu LCMS2020 | Ultimate XB-C18 2.1 * 30 mm, 3 um | A: water(4 L) + TFA (1.5 mL) B: acetonitrile(4 L) + TFA(0.75 mL) | from 10% B to 80% B in 3 minutes and holding at 80% for 0.5 minutes, to 10% B in 0.01 min held for 0.49 min | 1 | 50 | 4 |

TABLE 1-continued

| Method | Instrument | Column | Mobile phase | Gradient | Flow (mL/min) | Col. T (° C.) | Run time |
|---|---|---|---|---|---|---|---|
| D | Agilent 1260 Infinity II | Agilent Poroshell 120, EC-C18, 4.6 × 100 mm – 4 µm | A: 0.1% FA in H2O, B: 0.05% FA in MeCN | 2.0 min 98% A, from 98% A to 0% A in 10 min, hold for 3.4 min. | 1 | 50 | 15.4 |
| E | Shimadzu LCMS2020 | Kinetex EVO C18 (30 × 3 mm × 3 um) | Mobile phase A: Water/6.5 mM NH4HCO3 + Ammonia Hydroxide(pH = 10), Mobile phase B: Acetonitrile | 10% B at 0.01 min, to 95% B at 1.20 min, hold to 1.80 min, 10% B at 1.82 min | 1.2 | 40 | 2 |

Biological Assays

THR Biochemical Assay (sAsay 1)

The TR-FRET thyroid receptor beta coactivator assay was used with slight, optimized modifications of the manufacturer's protocol (Invitrogen). The assay uses a terbium-labeled anti-GST antibody, a glutathione-S-transferase (GST) tagged human thyroid receptor, beta or alpha, ligand-binding domain (LBD), and a fluorescein labeled SRC2-2 coactivator peptide. The antibody interacts with the LBD, where the agonist also binds, resulting in increased affinity for the SRC2-2 coactivator peptide causing energy transfer of the acceptor fluorophore and a FRET emission shift from 495 to 520 nm. The energy transfer is detected as an increase in the fluorescence emission of the fluorescein acceptor, and a decrease in the fluorescence emission of the terbium donor. The assay is performed in a 384-well black plate in a final volume of 20 µL. Serial dilution of various test agonists was performed in DMSO (1% final DMSO concentration) and added to the test plate. Thyroid receptor beta LBD is added to the plate at a final concentration of 1 nM, followed by the mixture of the fluorescein labeled SRC2-2 coactivator peptide, and the terbium-labeled anti-GST antibody at final concentrations of 200 nM and 2 nM respectively. The assay is incubated for 1 h at rt protected from light. The TR-FRET is then measured on a Victor multilabel reader (Perkin Elmer) using an excitation wavelength of 340 nm with emission filters of 495 nm and 520 nm. The assay is quantified by expressing a ratio (520:495) of the intensities, and the resulting activation curves; $EC_{50}$ values were generated using a sigmoidal dose response (variable slope) equation in GraphPad™ Prism 8.0.

Huh-7 Differential Gene Expression (Assay 2)

Serum Stripping

AG® 1-X8 Anion Exchange Resin (analytical grade, 200-400 mesh, chloride form; 1401451, Bio-Rad) was pre-washed with distilled water three times; water was separated from resin via centrifugation. Fetal bovine serum (FBS) was incubated with washed resin (50 mg resin/mL FBS; resin weight is dry weight of resin prior to washing) for 5 hr at room temperature on a rotor. The FBS was separated from the resin via centrifugation and incubated with new, washed resin for 18h at room temperature on a rotor. The resin-treated FBS (rFBS) was separated via centrifugation and then sterilized via filtration (0.22 µM PES membrane).

Cell Culture and Drug Treatment

Huh-7 cells were cultured in DMEM (10-013-CM, Corning) supplemented with 10% FBS and 1% Pen-Strep at 37° C. under 5% CO2. When 70-80% confluence was reached, the cells were removed by trypsinization. The medium was aspirated from the cell culture dish, the cell monolayer was washed with 1× PBS, and 0.05% trypsin, 0.53 mM EDTA (25-052-CV, Corning) solution was added to the dish. After 3 min incubation, the cells were detached completely by repeatedly pipetting solution onto the monolayer. Equal volume of DMEM supplemented with 10% rFBS and 1% Pen-Strep (TH-depleted DMEM) was added to the dish to inactivate the trypsin. The cell suspension was centrifuged at 350×g at room temperature for 3 min. The supernatant was aspirated out and the cell pellet was resuspended in TH-depleted DMEM. Cell density was quantified with a Vi-CELL XR Cell Viability Analyzer (Beckman Coulter) and cells were seeded onto Collagen I 96-well plates (356407, Corning) at 50,000 cells/well in 150 µL TH-depleted DMEM; the outer, perimeter wells were not used to avoid edge effect. After 24 hr incubation, the media was replaced with treatment media. All compounds were serially diluted in DMSO and final concentrations were reached by dilution in TH-depleted DMEM (0.1% DMSO). The cells were incubated in treatment media for 24 hr. Treatments were performed in biological duplicates.

Cell Lysis and RT-qPCR

After 24 h in treatment media, the cells were lysed directly on the culture plates and cDNA was produced using the TaqMan™ Fast Advanced Cells-to-CT™ Kit (A35374, Invitrogen) and following the manufacturer's protocol. RT-qPCR for CPT1A (Hs00912671_m1) and two housekeeping genes, ACTB (Hs01060665_g1) and TFG (Hs02832013_g1), was performed using TaqMan™ Fast Advanced Master Mix. RT-qPCR reactions were run on the qTOWER[3] 84 G (Analytik Jena) in technical duplicates.

Data Analysis

ΔRn values were obtained from the qPCRsoft384 1.0 software and CPT1A gene expression was quantified via the 2ΔΔCt method. Dose-response curves were generated using GraphPad Prism 8 using four parameter logistic equation without top constraint to derive $EC_{50}$ and $E_{max}$.

Compounds of Formula I are active as THR-alpha/beta agonists as shown in Table 2, where: for Assay 1: 'A' indicates an $EC_{50}$<50 nM, 'B' indicates an $EC_{50}$ of ≥50 nM and <250 nM, 'C' indicates an $EC_{50}$≥250 nM and <1000 nM, 'D' indicates an $EC_{50}$≥1000 nM and <25000 nM, and 'E' indicates an $EC_{50}$>25000 nM.

TABLE 2

| Compound number | Activity category Assay 1 | |
|---|---|---|
| | THRα | THRβ |
| 1 | C | A |
| 2 | B | A |
| 3 | A | A |

TABLE 2-continued

| Compound number | Activity category Assay 1 | |
|---|---|---|
| | THRα | THRβ |
| 4 | A | A |
| 5 | A | A |
| 6 | D | B |
| 7 | E | D |
| 8 | E | A |
| 9 | E | A |
| 10 | E | A |
| 11 | E | A |

Compounds of Formula I have activity as THR-alpha/beta agonists as shown in Table 3, where: for Assay 1: 'C' indicates an $E_{max}$<50%, 'B' indicates an $E_{max}$≥50%, and <75%, 'A' indicates an $E_{max}$≥75%.

TABLE 3

| Compound number | Activity category Assay 1 | |
|---|---|---|
| | THRα | THRβ |
| 1 | C | C |
| 2 | C | C |
| 3 | C | C |
| 4 | C | B |
| 5 | C | C |
| 6 | C | C |
| 7 | C | C |
| 8 | C | C |
| 9 | C | C |
| 10 | C | C |
| 11 | C | C |

Compounds of Formula I have activity as THR agonists as shown in Table 4, where: for Assay 2 in the $EC_{50}$ column: 'A' indicates an $EC_{50}$<100 nM, 'B' indicates an $EC_{50}$ of ≥100 nM and <1000 nM, 'C' indicates an $EC_{50}$≥1000 nM. In the Emax column, 'C' indicates an $E_{max}$<50%, 'B' indicates an $E_{max}$≥50%, and <75%, 'A' indicates an $E_{max}$≥75%.

TABLE 4

| Compound | Activity category Assay 2 | |
|---|---|---|
| | $EC_{50}$ | $E_{max}$ |
| Reference(T3) | A | A |
| 1 | B | A |
| 2 | A | A |
| 6 | B | C |
| 11 | B | C |

Diet-Induced Obese (DIO) Mouse Model of NASH

C57BL/6J mice are fed a high-fat diet for 10 weeks to induce obesity and injected intraperitoneally twice weekly with carbon tetrachloride ($CCl_4$) for an additional 4 weeks to induce fibrosis. Mice fed a normal chow diet are used as healthy controls. Concomitant with $CCl_4$ dosing, mice are treated with vehicle or with a compound disclosed herein, administered by oral gavage once daily for 28 days. Drug exposure is measured in a separate experiment in lean male C57BL/6J mice. Livers of mice in the NASH study are harvested and evaluated for liver steatosis and fibrosis by histology and whole transcriptome analysis in the liver using RNA sequencing. Target engagement is confirmed by monitoring expression of TRβ-regulated genes.

Human Clinical Study: NASH

In a randomized, double-blind, placebo-controlled study, adult patients (with biopsy confirmed NASH (fibrosis stages 1-3) and hepatic fat fraction of at least 10% at baseline when assessed by MRI-proton density fat fraction (MRI-PDFF) are administered a compound disclosed herein or placebo. Serial hepatic fat measurements are obtained at weeks 12 and 36, and a second liver biopsy is obtained at week 36. The primary endpoint is relative change in MRI-PDFF assessed hepatic fat compared with placebo at week 12 in patients who have both a baseline and week 12 MRI-PDFF.

REFERENCES

1. Younossi, Z M, Koenig, A B, Abdelatif, D, Fazel, Y, Henry, L, Wymer, M. Global epidemiology of nonalcoholic fatty liver disease-Meta-analytic assessment of prevalence, incidence, and outcomes. Hepatology, 2016, 64(1):73e84.
2. Gastroenterology. 2012 June; 142(7): 1592-609. doi: 10.1053/j.gastro.2012.04.001. Epub 2012 May 15.
3. Serfaty, L., Lemoine, M. Definition and natural history of metabolic steatosis: clinical aspects of NAFLD, NASH and cirrhosis. Diabetes and Metabolism, 2008, 34 (6 Pt 2):634e637.
4. Hepatology. 2012 October; 56(4): 1580-1584. doi: 10.1002/hep.26031
5. Dulai, P S, Singh, S, Patel, J, Soni, M, Prokop, L J, Younossi, Z, et al.. Increased risk of mortality by fibrosis stage in nonalcoholic fatty liver disease: systematic review and meta-analysis. Hepatology, 2017, 65(5):1557e1565.
6. Younossi, Z M, Loomba, R, Rinella, M E, Bugianesi, E, Marchesini, G, Neuschwander-Tetri, B A, et al. Current and future therapeutic regimens for non-alcoholic fatty liver disease (NAFLD) and non-alcoholic steatohepatitis (NASH). Hepatology, 2018, 68(1): 349e360.
7. Harvey C B, Williams G R. Mechanism of thyroid hormone action. Thyroid, 2002 June; 12(6):441-6.
8. Bookout A L, Jeong Y, Downes M, Yu R T, Evans R M, Mangelsdorf D J. Anatomical profiling of nuclear receptor expression reveals a hierarchical transcriptional network. Cell, 2006, 126:789-799
9. Flamant F, Baxter J D, Forrest D, Refetoff S, Samuels H H, Scanlan T S, Vennstrom B, Samarut J. International union of pharmacology. LIX. The pharmacology and classification of the nuclear receptor superfamily: thyroid hormone receptors. Pharmacol. Rev., 2006, 58:705-711
10. Haning H, Woltering M, Mueller U, Schmidt G, Schmeck C, Voehringer V, Kretschmer A, Pernerstorfer J. Bioorg. Med Chem Lett., 2005 Apr 1, 15(7): 1835-40. Novel heterocyclic thyromimetics.
11. Hirano T, Kagechika H. Thyromimetics: a review of recent reports and patents (2004-2009). Expert Opin Ther Pat., 2010 Feb; 20(2):213-28. doi: 10.1517/13543770903567069.
12. Kowalik MA , Columbano A, Perra A. Thyroid Hormones, Thyromimetics and Their Metabolites in the Treatment of Liver Disease. Front Endocrinol (Lausanne), 2018 Jul. 10; 9:382. doi: 10.3389/fendo.2018.00382. eCollection 2018.
13. Erion M D, Cable E E, Ito B R, Jiang H, Fujitaki J M, Finn P D, Zhang B H, Hou J, Boyer S H, van Poelje P D, Linemeyer D L. Targeting thyroid hormone receptor-beta agonists to the liver reduces cholesterol and triglycerides and improves the therapeutic index. Proc Natl Acad Sci U S A., 2007 Sep. 25; 104(39):15490-5. Epub 2007 Sep. 18.

14. Hartley MD , Kirkemo L L, Banerji T, Scanlan T S. A Thyroid Hormone-Based Strategy for Correcting the Biochemical Abnormality in X-Linked Adrenoleukodystrophy. Endocrinology 2017, 158(5), p1328-1338. doi: 10.1210/en.2016-1842.

15. Milanesi A, Brent G A. Beam Me In: Thyroid Hormone Analog Targets Alternative Transporter in Mouse Model of X-Linked Adrenoleukodystrophy. Endocrinology 2017, 158, p1116-1119. doi: 10.1210/en.2017-00206.

Embodiments

Embodiment 1. A compound of Formula I:

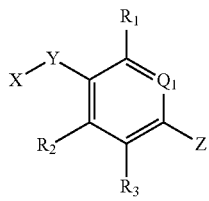

Formula I or a stereoisomer or a tautomer thereof, or a pharmaceutically acceptable salt thereof, wherein $Q_1$ is CH or N;

$R_1$ and $R_2$ are each independently selected from hydrogen, halogen, cyclopropyl, and $C_{1-3}$ alkyl optionally substituted with 1 to 5 fluorine;

$R_3$ is selected from hydrogen, deuterium, halogen, —CN, alkoxy, and $C_{1-6}$ alkyl; or $R_2$ and $R_3$ taken together along with the carbon atoms to which they are attached form a 4- to 6-membered carbocyclic ring or a four- to six-membered heterocyclic ring;

X is an optionally substituted 6- to 10-membered heterocycle;

Y is O or $CH_2$;

Z is selected from the group consisting of:

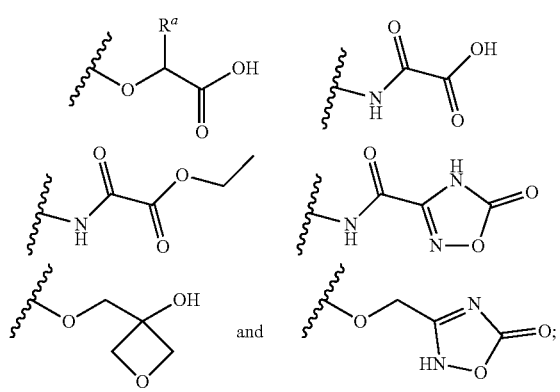

and $R^a$ is selected from hydrogen, methyl, and fluorine.

Embodiment 2. The compound of embodiment 1, or a stereoisomer or a tautomer thereof, or a pharmaceutically acceptable salt thereof, wherein X is:

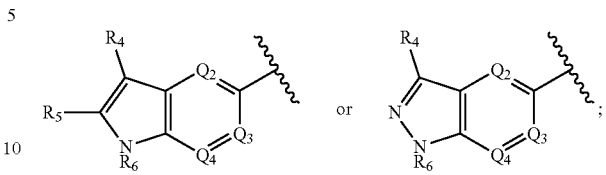

wherein $R_4$ is selected from hydrogen; $C_1$-$C_6$ alkyl; a non-aromatic $C_3$-$C_{12}$ carbocyclic ring; a $C_6$-$C_{10}$ aryl group; a (carbocyclic)alkyl group; and an aralkyl group; and $R_4$ is optionally substituted with one to three $R_k$ independently selected from halogen, —CN, $C_1$-$C_6$ alkyl, $C_1$-$C_6$ alkoxy, $C_1$-$C_6$ haloalkyl, and $C_1$-$C_6$ haloalkoxy;

$R_5$ is selected from hydrogen; halogen; $C_1$-$C_6$ alkyl optionally substituted with halogen or $C_1$-$C_6$ alkoxy; and $C_3$-$C_9$ cycloalkyl optionally substituted with halogen or $C_1$-$C_6$ alkoxy;

$R_6$ is hydrogen or $C_1$-$C_3$ alkyl; and $Q_2$, $Q_3$, and $Q_4$ are each independently selected from CH or N, and at least one of $Q_2$, $Q_3$, and $Q_4$ must be N.

Embodiment 3. The compound of embodiment 2, or a stereoisomer or a tautomer thereof, or a pharmaceutically acceptable salt thereof, wherein X is

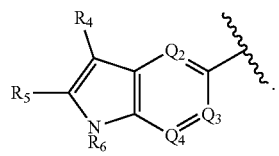

Embodiment 4. The compound of embodiment 3, or a stereoisomer or a tautomer thereof, or a pharmaceutically acceptable salt thereof, wherein $R_4$ is $C_1$-$C_6$ alkyl.

Embodiment 5. The compound of any one of embodiments 2-4, or a stereoisomer or a tautomer thereof, or a pharmaceutically acceptable salt thereof, wherein $R_5$ is hydrogen.

Embodiment 6. The compound of any one of embodiments 2-4, or a stereoisomer or a tautomer thereof, or a pharmaceutically acceptable salt thereof, wherein $R_5$ is $C_1$-$C_6$ alkyl.

Embodiment 7. The compound of embodiment 1, or a stereoisomer or a tautomer thereof, or a pharmaceutically acceptable salt thereof, wherein X is:

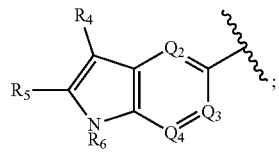

$R_4$ and $R_5$ taken together along with the carbon atoms to which they are attached form a 4- to 6-membered carbocyclic ring;

$R_6$ is hydrogen or $C_1$-$C_3$ alkyl; and $Q_2$, $Q_3$, and $Q_4$ are each independently selected from CH or N.

Embodiment 8. The compound of any one of embodiments 2-7, or a stereoisomer or a tautomer thereof, or a pharmaceutically acceptable salt thereof, wherein $Q_2$ is N.

Embodiment 9. The compound of any one of embodiments 2-8, or a stereoisomer or a tautomer thereof, or a pharmaceutically acceptable salt thereof, wherein $Q_3$ and $Q_4$ are CH.

Embodiment 10. The compound of any one of embodiments 1-9, or a stereoisomer or a tautomer thereof, or a pharmaceutically acceptable salt thereof, wherein $Q_1$ is CH.

Embodiment 11. The compound of any one of embodiments 1-9, or a stereoisomer or a tautomer thereof, or a pharmaceutically acceptable salt thereof, wherein $Q_1$ is N.

Embodiment 12. The compound of any one of embodiments 1-11, or a stereoisomer or a tautomer thereof, or a pharmaceutically acceptable salt thereof, wherein $R_1$ and $R_2$ are each independently selected from halogen, cyclopropyl, and $C_{1-3}$ alkyl optionally substituted with 1 to 5 fluorine.

Embodiment 13. The compound of any one of embodiments 1-12, or a stereoisomer or a tautomer thereof, or a pharmaceutically acceptable salt thereof, wherein $R_1$ and $R_2$ are each independently $C_{1-3}$ alkyl.

Embodiment 14. The compound of any one of embodiments 1-13, or a stereoisomer or a tautomer thereof, or a pharmaceutically acceptable salt thereof, wherein $R_1$ and $R_2$ are both $CH_3$.

Embodiment 15. The compound of any one of embodiments 1-14, or a stereoisomer or a tautomer thereof, or a pharmaceutically acceptable salt thereof, wherein $R_3$ is hydrogen or $C_{1-6}$ alkyl.

Embodiment 16. The compound of any one of embodiments 1-14, or a stereoisomer or a tautomer thereof, or a pharmaceutically acceptable salt thereof, wherein $R_3$ is hydrogen or $CH_3$.

Embodiment 17. The compound of any one of embodiments 1-16, or a stereoisomer or a tautomer thereof, or a pharmaceutically acceptable salt thereof, wherein Y is $CH_2$.

Embodiment 18. The compound of any one of embodiments 1-16, or a stereoisomer or a tautomer thereof, or a pharmaceutically acceptable salt thereof, wherein Y is O.

Embodiment 19. The compound of any one of embodiments 1-18, or a stereoisomer or a tautomer thereof, or a pharmaceutically acceptable salt thereof, wherein Z is selected from the group consisting of:

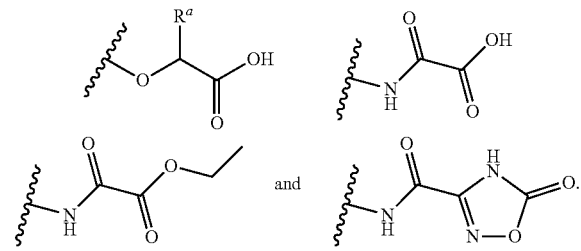

Embodiment 20. A compound selected from the group consisting of:
2-(4-((3-isopropyl-1H-pyrrolo[3,2-b]pyridin-5-yl)methyl)-2,3,5-trimethylphenoxy)acetic acid;
2-(4-((3-isopropyl-1H-pyrrolo[3,2-b]pyridin-5-yl)methyl)-3,5-dimethylphenoxy)acetic acid;
N-(4-((3-isopropyl-1H-pyrrolo[3,2-b]pyridin-5-yl)methyl)-3,5-dimethylphenyl)-5-oxo-4,5-dihydro-1,2,4-oxadiazole-3-carboxamide;
2-((4-((3-isopropyl-1H-pyrrolo[3,2-b]pyridin-5-yl)methyl)-3,5-dimethylphenyl)amino)-2-oxoacetic acid; and
ethyl 2-((4-((3-isopropyl-1H-pyrrolo[3,2-b]pyridin-5-yl)methyl)-3,5-dimethylphenyl)amino)-2-oxoacetate;
or a stereoisomer or a tautomer thereof, or a pharmaceutically acceptable salt thereof.

Embodiment 21. A pharmaceutical composition comprising the compound of any one of embodiments 1-20, or the stereoisomer or the tautomer thereof, or the pharmaceutically acceptable salt thereof, and at least one pharmaceutically acceptable excipient.

Embodiment 22. A method of treating a disorder or disease in a subject in need thereof, the method comprising administering to the subject a therapeutically effective amount of the compound of any one of embodiments 1-20, or the stereoisomer or the tautomer thereof, or the pharmaceutically acceptable salt thereof, or a therapeutically effective amount of the pharmaceutical composition of embodiment 21, wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 23. Use of the compound of any one of embodiments 1-20, or the stereoisomer or the tautomer thereof, or the pharmaceutically acceptable salt thereof, for the manufacture of a medicament for the treatment of a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 24. A compound of any one of embodiments 1-20, or a stereoisomer or a tautomer thereof, or a pharmaceutically acceptable salt thereof, for use in treating a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 25. A composition of embodiment 21 for use in treating a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 26. A method of treating a thyroid hormone receptor related disorder in a patient, the method comprising the steps of:
identifying a patient in need of treatment for the thyroid hormone receptor related disorder, and administering to the patient, or contacting the patient with, the compound of any one of embodiments 1-20, or the stereoisomer or the tautomer thereof, or the pharmaceutically acceptable salt thereof, or a therapeutically effective amount of the pharmaceutical composition of embodiment 21.

Embodiment 27. The method of embodiment 26, wherein the thyroid hormone receptor related disorder is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 28. A method of selectively modulating the activity of a thyroid hormone receptor beta (THR-β) comprising contacting the compound of any one of embodiments 1-20, or the stereoisomer or the tautomer thereof, or the pharmaceutically acceptable salt thereof, with the thyroid hormone receptor.

Embodiment 29. The method of embodiment 28, wherein the contacting is in vitro or ex vivo.

Embodiment 30. The method of embodiment 28, wherein the contacting is in vivo.

Embodiment 31. A compound of any one of embodiments 1-20, or a stereoisomer or a tautomer thereof, or a pharmaceutically acceptable salt thereof, for use in selectively modulating the activity of a thyroid hormone receptor beta (THR-β).

Embodiment 32. A composition of embodiment 21 for use in selectively modulating the activity of a thyroid hormone receptor beta (THR-β).

Embodiment 33. A compound of Formula I':

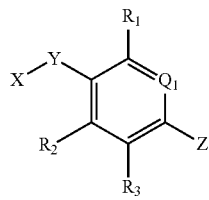

Formula I' or a stereoisomer or a tautomer thereof, or a pharmaceutically acceptable salt thereof, wherein $Q_1$ is CH or N;

$R_1$ and $R_2$ are each independently selected from hydrogen, halogen, cyclopropyl, and $C_{1-3}$ alkyl optionally substituted with 1 to 5 fluorine;

$R_3$ is selected from hydrogen, deuterium, halogen, —CN, $C_{1-10}$ alkoxy, and $C_{1-6}$ alkyl; or $R_2$ and $R_3$ taken together along with the carbon atoms to which they are attached form a 4- to 6-membered carbocyclic ring or a four- to six-membered heterocyclic ring;

X is

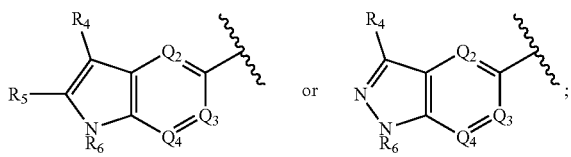

$R_4$ is selected from hydrogen; $C_1$-$C_6$ alkyl; a non-aromatic $C_3$-$C_{12}$ carbocyclic ring; a $C_6$-$C_{10}$ aryl group; a (carbocyclic)alkyl group; and an aralkyl group; wherein $R_4$ is optionally substituted with one to three $R_k$ independently selected from halogen, —CN, $C_1$-$C_6$ alkyl, $C_1$-$C_6$ alkoxy, $C_1$-$C_6$ haloalkyl, and $C_1$-$C_6$ haloalkoxy; and $R_5$ is selected from hydrogen; halogen; $C_1$-$C_6$ alkyl optionally substituted with halogen or $C_1$-$C_6$ alkoxy; and $C_3$-$C_9$ cycloalkyl optionally substituted with halogen or $C_1$-$C_6$ alkoxy; or $R_4$ and $R_5$ taken together along with the carbon atoms to which they are attached form a 4- to 6-membered carbocyclic ring;

$R_6$ is hydrogen or $C_1$-$C_3$ alkyl;

$Q_2$, $Q_3$, and $Q_4$ are each independently selected from CH or N, and at least one of $Q_2$, $Q_3$, and $Q_4$ must be N;

Y is O or $CH_2$;

Z is selected from the group consisting of:

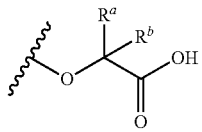 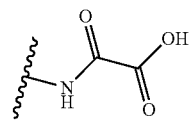

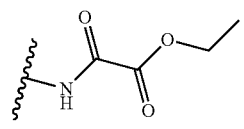 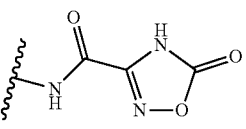

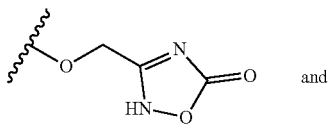 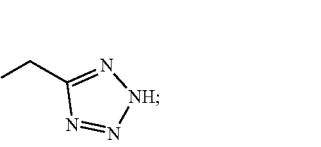 and

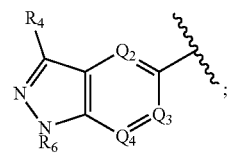

and $R^a$ and $R^b$ are each independently selected from hydrogen, methyl, and fluorine;

with the proviso that when X is

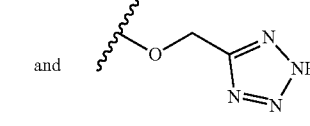

$Q_1$ is CH; $R_1$ and $R_2$ are each independently halogen; $R_3$ is hydrogen; $R_4$ is $C_1$-$C_6$ alkyl; $R_6$ is hydrogen; $Q_2$ is CH; $Q_3$ is CH; $Q_4$ is N; and Y is O; then Z is selected from the group consisting of:

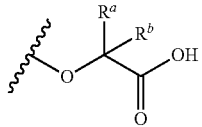 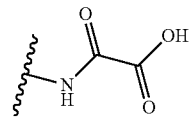

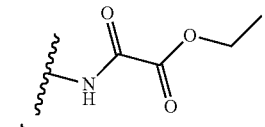 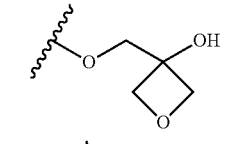

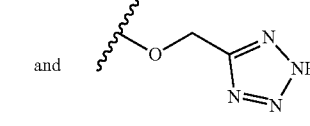 and 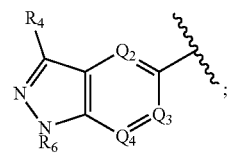

Embodiment 34. The compound of Embodiment 33, or a stereoisomer or a tautomer thereof, or a pharmaceutically acceptable salt thereof, wherein X is

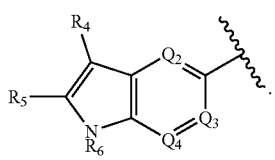

Embodiment 35. The compound of Embodiment 33 or Embodiment 34, or a stereoisomer or a tautomer thereof, or a pharmaceutically acceptable salt thereof, wherein $R_4$ is $C_1$-$C_6$ alkyl.

Embodiment 36. The compound of Embodiment 33 or Embodiment 34, or a stereoisomer or a tautomer thereof, or a pharmaceutically acceptable salt thereof, wherein $R_4$ is isopropyl.

Embodiment 37. The compound of any one of Embodiments 33-36, or a stereoisomer or a tautomer thereof, or a pharmaceutically acceptable salt thereof, wherein $R_5$ is hydrogen.

Embodiment 38. The compound of any one of Embodiments 33-36, or a stereoisomer or a tautomer thereof, or a pharmaceutically acceptable salt thereof, wherein $R_5$ is $C_1$-$C_6$ alkyl.

Embodiment 39. The compound of any one of Embodiments 33-38, or a stereoisomer or a tautomer thereof, or a pharmaceutically acceptable salt thereof, wherein X is:

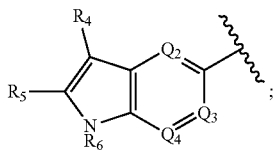

$R_4$ is selected from hydrogen; $C_1$-$C_6$ alkyl; a non-aromatic $C_3$-$C_{12}$ carbocyclic ring; a $C_6$-$C_{10}$ aryl group; a (carbocyclic)alkyl group; and an aralkyl group; wherein $R_4$ is optionally substituted with one to three $R_k$ independently selected from halogen, —CN, $C_1$-$C_6$ alkyl, $C_1$-$C_6$ alkoxy, $C_1$-$C_6$ haloalkyl, and $C_1$-$C_6$ haloalkoxy;

$R_5$ is selected from hydrogen; halogen; $C_1$-$C_6$ alkyl optionally substituted with halogen or $C_1$-$C_6$ alkoxy; and $C_3$-$C_9$ cycloalkyl optionally substituted with halogen or $C_1$-$C_6$ alkoxy;

$R_6$ is hydrogen or $C_1$-$C_3$ alkyl; and $Q_2$, $Q_3$, and $Q_4$ are each independently selected from CH or N, and at least one of $Q_2$, $Q_3$, and $Q_4$ must be N.

Embodiment 40. The compound of any one of Embodiments 33-38, or a stereoisomer or a tautomer thereof, or a pharmaceutically acceptable salt thereof, wherein X is:

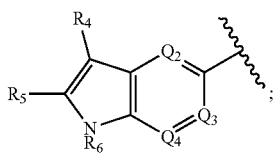

$R_4$ and $R_5$ taken together along with the carbon atoms to which they are attached form a 4- to 6-membered carbocyclic ring;

$R_6$ is hydrogen or $C_1$-$C_3$ alkyl; and $Q_2$, $Q_3$, and $Q_4$ are each independently selected from CH or N, and at least one of $Q_2$, $Q_3$, and $Q_4$ must be N.

Embodiment 41. The compound of any one of Embodiments 33-40, or a stereoisomer or a tautomer thereof, or a pharmaceutically acceptable salt thereof, wherein $Q_2$ is N.

Embodiment 42. The compound of any one of Embodiments 33-41, or a stereoisomer or a tautomer thereof, or a pharmaceutically acceptable salt thereof, wherein $Q_3$ and $Q_4$ are CH.

Embodiment 43. The compound of any one of Embodiments 33-42, or a stereoisomer or a tautomer thereof, or a pharmaceutically acceptable salt thereof, wherein the compound has the chemical structure of Formula I' a:

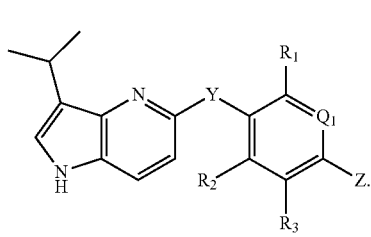

Formula I'a

Embodiment 44. The compound of any one of Embodiments 33-43, or a stereoisomer or a tautomer thereof, or a pharmaceutically acceptable salt thereof, wherein $Q_1$ is CH.

Embodiment 45. The compound of any one of Embodiments 33-43, or a stereoisomer or a tautomer thereof, or a pharmaceutically acceptable salt thereof, wherein $Q_1$ is N.

Embodiment 46. The compound of any one of Embodiments 33-45, or a stereoisomer or a tautomer thereof, or a pharmaceutically acceptable salt thereof, wherein $R_1$ and $R_2$ are each independently selected from halogen, cyclopropyl, and $C_{1-3}$ alkyl optionally substituted with 1 to 5 fluorine.

Embodiment 47. The compound of any one of Embodiments 33-46, or a stereoisomer or a tautomer thereof, or a pharmaceutically acceptable salt thereof, wherein $R_1$ and $R_2$ are each independently $C_{1-3}$ alkyl.

Embodiment 48. The compound of any one of Embodiments 33-46, or a stereoisomer or a tautomer thereof, or a pharmaceutically acceptable salt thereof, wherein $R_1$ and $R_2$ are both $CH_3$.

Embodiment 49. The compound of any one of Embodiments 33-48, or a stereoisomer or a tautomer thereof, or a pharmaceutically acceptable salt thereof, wherein $R_3$ is hydrogen or $C_{1-6}$ alkyl.

Embodiment 50. The compound of any one of Embodiments 33-48, or a stereoisomer or a tautomer thereof, or a pharmaceutically acceptable salt thereof, wherein $R_3$ is hydrogen or $CH_3$.

Embodiment 51. The compound of any one of Embodiments 33-48, or a stereoisomer or a tautomer thereof, or a pharmaceutically acceptable salt thereof, wherein $R_3$ is hydrogen.

Embodiment 52. The compound of any one of Embodiments 33-48, or a stereoisomer or a tautomer thereof, or a pharmaceutically acceptable salt thereof, wherein $R_3$ is $CH_3$.

Embodiment 53. The compound of any one of Embodiments 33-45, or a stereoisomer or a tautomer thereof, or a pharmaceutically acceptable salt thereof, wherein $R_1$, $R_2$, and $R_3$ are each independently $C_{1-3}$ alkyl.

Embodiment 54. The compound of any one of Embodiments 33-45, or a stereoisomer or a tautomer thereof, or a pharmaceutically acceptable salt thereof, wherein $R_1$, $R_2$, and $R_3$ are $CH_3$.

Embodiment 55. The compound of any one of Embodiments 33-54, or a stereoisomer or a tautomer thereof, or a pharmaceutically acceptable salt thereof, wherein Y is CH$_2$.

Embodiment 56. The compound of any one of Embodiments 33-54, or a stereoisomer or a tautomer thereof, or a pharmaceutically acceptable salt thereof, wherein Y is O.

Embodiment 57. The compound of any one of Embodiments 33-56, or a stereoisomer or a tautomer thereof, or a pharmaceutically acceptable salt thereof, wherein Z is selected from the group consisting of:

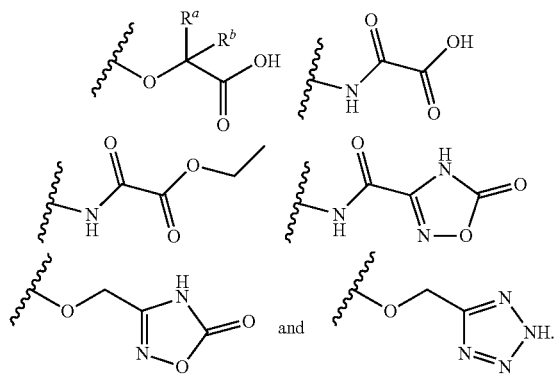

Embodiment 58. The compound of any one of Embodiments 33-56, or a stereoisomer or a tautomer thereof, or a pharmaceutically acceptable salt thereof, wherein Z is selected from the group consisting of:

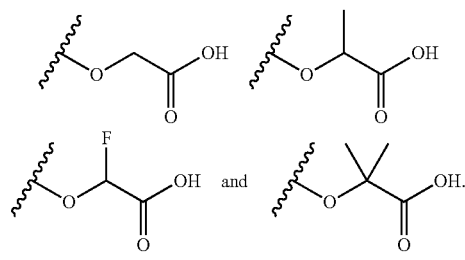

Embodiment 59. A compound selected from the group consisting of:
2-(4-((3-isopropyl-1H-pyrrolo[3,2-b]pyridin-5-yl)methyl)-2,3,5-trimethylphenoxy)acetic acid;
2-(4-((3-isopropyl-1H-pyrrolo[3,2-b]pyridin-5-yl)methyl)-3,5-dimethylphenoxy)acetic acid;
N-(4-((3-isopropyl-1H-pyrrolo[3,2-b]pyridin-5-yl)methyl)-3,5-dimethylphenyl)-5-oxo-4,5-dihydro-1,2,4-oxadiazole-3-carboxamide;
2-((4-((3-isopropyl-1H-pyrrolo[3,2-b]pyridin-5-yl)methyl)-3,5-dimethylphenyl)amino)-2-oxoacetic acid;
ethyl 2-((4-((3-isopropyl-1H-pyrrolo[3,2-b]pyridin-5-yl)methyl)-3,5-dimethylphenyl)amino)-2-oxoacetate; [[5-([3-isopropyl-1H-pyrrolo[3,2-b]pyridin-5-yl]methyl)-3,4,6-trimethylpyridin-2-yl]oxy]acetic acid;
4-[[3-isopropyl-1-(4-methylbenzenesulfonyl)pyrrolo[3,2-b]pyridin-5-yl]methyl]-2,3,5-trimethylphenol;
2-(4-((3-isopropyl-1H-pyrrolo[3,2-b]pyridin-5-yl)methyl)-2,3,5-trimethylphenoxy)propanoic acid;
2-(4-((3-isopropyl-1H-pyrrolo[3,2-b]pyridin-5-yl)methyl)-2,3,5-trimethylphenoxy)-2-methylpropanoic acid;
2-fluoro-2-(4-((3-isopropyl-1H-pyrrolo[3,2-b]pyridin-5-yl)methyl)-2,3,5-trimethylphenoxy)acetic acid;
5-(4-((2H-tetrazol-5-yl)methoxy)-2,3,6-trimethylbenzyl)-3-isopropyl-1H-pyrrolo[3,2-b]pyridine; and
3-((3-isopropyl-1H-pyrrolo[3,2-b]pyridin-5-yl)methyl)-2,3,5-trimethylphenoxy)methyl)-1,2,4-oxadiazol-5(4H)-one;
or a stereoisomer or a tautomer thereof, or a pharmaceutically acceptable salt thereof.

Embodiment 60. A pharmaceutical composition comprising the compound of any one of Embodiments 33-59, or the stereoisomer or the tautomer thereof, or the pharmaceutically acceptable salt thereof, and at least one pharmaceutically acceptable excipient.

Embodiment 61. A method of treating a disorder or disease in a subject in need thereof, the method comprising administering to the subject a therapeutically effective amount of the compound of any one of Embodiments 33-59, or the stereoisomer or the tautomer thereof, or the pharmaceutically acceptable salt thereof, or a therapeutically effective amount of the pharmaceutical composition of Embodiment 60, wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 62. Use of the compound of any one of Embodiments 33-59, or the stereoisomer or the tautomer thereof, or the pharmaceutically acceptable salt thereof, for the manufacture of a medicament for the treatment of a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 63. A compound of any one of Embodiments 33-59, or a stereoisomer or a tautomer thereof, or a pharmaceutically acceptable salt thereof, for use in treating a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 64. A composition of Embodiment 60 for use in treating a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 65. A method of treating a thyroid hormone receptor related disorder in a patient, the method comprising the steps of:
identifying a patient in need of treatment for the thyroid hormone receptor related disorder, and administering to the patient, or contacting the patient with, the compound of any one of Embodiments 33-59, or the stereoisomer or the tautomer thereof, or the pharmaceutically acceptable salt thereof, or a therapeutically effective amount of the pharmaceutical composition of Embodiment 60.

Embodiment 66. The method of Embodiment 65, wherein the thyroid hormone receptor related disorder is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 67. A method of selectively modulating the activity of a thyroid hormone receptor beta (THR-β) comprising contacting the compound of any one of Embodiments 33-59, or the stereoisomer or the tautomer thereof, or the pharmaceutically acceptable salt thereof, with the thyroid hormone receptor.

Embodiment 68. The method of Embodiment 67, wherein the contacting is in vitro or ex vivo.

Embodiment 69. The method of Embodiment 67, wherein the contacting is in vivo.

Embodiment 70. A compound of any one of Embodiments 33-59, or a stereoisomer or a tautomer thereof, or a pharmaceutically acceptable salt thereof, for use in selectively modulating the activity of a thyroid hormone receptor beta (THR-β).

Embodiment 71. A composition of Embodiment 60 for use in selectively modulating the activity of a thyroid hormone receptor beta (THR-β).

Embodiment 72. The method of Embodiment 65, wherein the compound of any one of Embodiments 33-59 or the stereoisomer or the tautomer thereof, or the pharmaceutically acceptable salt thereof, or a therapeutically effective amount of the pharmaceutical composition of Embodiment 60, is administered in combination with a KHK inhibitor, an FXR agonist, a SSAO inhibitor, a FASN inhibitor, or a SCD1 modulator.

Embodiment 73. The method of Embodiment 72, wherein the KHK inhibitor is PF-06835919; the FXR agonist is TERN-101 (LY2562175), Tropifexor, obeticholic acid (OCA), or ASC42; the SSAO inhibitor is TERN-201; the FASN inhibitor is ASC40; and the SCD1 modulator is aramchol.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

What is claimed is:

1. A compound of Formula I':

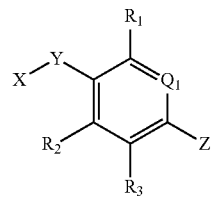

Formula I' or a stereoisomer or a tautomer thereof, or a pharmaceutically acceptable salt thereof, wherein $Q_1$ is CH or N;

$R_1$ and $R_2$ are each independently selected from hydrogen, halogen, cyclopropyl, and $C_{1-3}$ alkyl optionally substituted with 1 to 5 fluorine;

$R_3$ is selected from hydrogen, deuterium, halogen, —CN, $C_{1-10}$ alkoxy, and $C_{1-6}$ alkyl; or $R_2$ and $R_3$ taken together along with the carbon atoms to which they are attached form a 4- to 6-membered carbocyclic ring or a four- to six-membered heterocyclic ring;

X is

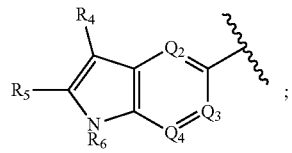
;

$R_4$ is selected from hydrogen; $C_1$-$C_5$ alkyl; a non-aromatic $C_3$-$C_{12}$ carbocyclic ring; a $C_6$-$C_{10}$ aryl group; a (carbocyclic)alkyl group; and an aralkyl group; wherein $R_4$ is optionally substituted with one to three $R_k$ independently selected from halogen, —CN, $C_1$-$C_6$ alkyl, $C_1$-$C_6$ alkoxy, $C_1$-$C_6$ haloalkyl, and $C_1$-$C_6$ haloalkoxy; and $R_5$ is selected from hydrogen; halogen; $C_1$-$C_6$ alkyl optionally substituted with halogen or $C_1$-$C_6$ alkoxy; and $C_3$-$C_9$ cycloalkyl optionally substituted with halogen or $C_1$-$C_6$ alkoxy; or R₄ and R₅ taken together along with the carbon atoms to which they are attached form a 4- to 6-membered carbocyclic ring;
R₆ is hydrogen or C₁-C₃ alkyl;
Q₂ is N, and Q₃, and Q₄ are each independently selected from CH or N;
Y is O or CH₂;
Z is selected from the group consisting of:

[chemical structures]

and
Rᵃ and Rᵇ are each independently selected from hydrogen, methyl, and fluorine.

2. The compound of claim 1, or a stereoisomer or a tautomer thereof, or a pharmaceutically acceptable salt thereof, wherein R₄ is C₁-C₆ alkyl.

3. The compound of claim 1, or a stereoisomer or a tautomer thereof, or a pharmaceutically acceptable salt thereof, wherein R₅ is hydrogen.

4. The compound of claim 1, or a stereoisomer or a tautomer thereof, or a pharmaceutically acceptable salt thereof, wherein X is:

[chemical structure]

R₄ is selected from hydrogen; C₁-C₆ alkyl; a non-aromatic C₃-C₁₂ carbocyclic ring; a C₆-C₁₀ aryl group; a (carbocyclic)alkyl group; and an aralkyl group; wherein R₄ is optionally substituted with one to three R_k independently selected from halogen, —CN, C₁-C₆ alkyl, C₁-C₆ alkoxy, C₁-C₆ haloalkyl, and C₁-C₆ haloalkoxy; and
R₅ is selected from hydrogen; halogen; C₁-C₆ alkyl optionally substituted with halogen or C₁-C₆ alkoxy; and C₃-C₉ cycloalkyl optionally substituted with halogen or C₁-C₆ alkoxy.

5. The compound of claim 1, or a stereoisomer or a tautomer thereof, or a pharmaceutically acceptable salt thereof, wherein Q₃ and Q₄ are CH.

6. The compound of claim 1, or a stereoisomer or a tautomer thereof, or a pharmaceutically acceptable salt thereof, wherein the compound has the chemical structure of Formula I'a:

Formula I'a

[chemical structure]

7. The compound of claim 1, or a stereoisomer or a tautomer thereof, or a pharmaceutically acceptable salt thereof, wherein R₁ and R₂ are each independently selected from halogen, cyclopropyl, and C₁₋₃ alkyl optionally substituted with 1 to 5 fluorine.

8. The compound of claim 1, or a stereoisomer or a tautomer thereof, or a pharmaceutically acceptable salt thereof, wherein Y is CH₂.

9. The compound of claim 1, or a stereoisomer or a tautomer thereof, or a pharmaceutically acceptable salt thereof, wherein Z is selected from the group consisting of:

[chemical structures]

10. The compound of claim 1, or a stereoisomer or a tautomer thereof, or a pharmaceutically acceptable salt thereof, wherein Z is selected from the group consisting of:

[chemical structures]

11. A compound selected from the group consisting of:
2-(4-((3-isopropyl-1H-pyrrolo[3,2-b]pyridin-5-yl)methyl)-2,3,5-trimethylphenoxy)acetic acid,
2-(4-((3-isopropyl-1H-pyrrolo[3,2-b]pyridin-5-yl)methyl)-3,5-dimethylphenoxy)acetic acid;

N-(4-((3-isopropyl-1H-pyrrolo[3,2-b]pyridin-5-yl)methyl)-3,5-dimethylphenyl)-5-oxo-4,5-dihydro-1,2,4-oxadiazole-3-carboxamide;
2-((4-((3-isopropyl-1H-pyrrolo[3,2-b]pyridin-5-yl)methyl)-3,5-dimethylphenyl)amino)-2-oxoacetic acid;
ethyl 2-((4-((3-isopropyl-1H-pyrrolo[3,2-b]pyridin-5-yl)methyl)-3,5-dimethylphenyl)amino)-2-oxoacetate;
[[5-([3-isopropyl-1H-pyrrolo[3,2-b]pyridin-5-yl]methyl)-3,4,6-trimethylpyridin-2-yl]oxy]acetic acid;
4-[[3-isopropyl-1-(4-methylbenzenesulfonyl)pyrrolo[3,2-b]pyridin-5-yl]methyl]-2,3,5-trimethylphenol;
2-(4-((3-isopropyl-1H-pyrrolo[3,2-b]pyridin-5-yl)methyl)-2,3,5-trimethylphenoxy)propanoic acid;
2-(4-((3-isopropyl-1H-pyrrolo[3,2-b]pyridin-5-yl)methyl)-2,3,5-trimethylphenoxy)-2-methylpropanoic acid;
2-fluoro-2-(4-((3-isopropyl-1H-pyrrolo[3,2-b]pyridin-5-yl)methyl)-2,3,5-trimethylphenoxy)acetic acid;
5-(4-((2H-tetrazol-5-yl)methoxy)-2,3,6-trimethylbenzyl)-3-isopropyl-1H-pyrrolo[3,2-b]pyridine; and
3-((4-((3-isopropyl-1H-pyrrolo[3,2-b]pyridin-5-yl)methyl)-2,3,5-trimethylphenoxy)methyl)-1,2,4-oxadiazol-5(4H)-one;
or a stereoisomer or a tautomer thereof, or a pharmaceutically acceptable salt thereof.

12. A pharmaceutical composition comprising the compound of claim 1, or the stereoisomer or the tautomer thereof, or the pharmaceutically acceptable salt thereof, and at least one pharmaceutically acceptable excipient.

* * * * *